United States Patent
Kothari et al.

(10) Patent No.: US 8,476,437 B2
(45) Date of Patent: Jul. 2, 2013

(54) PROCESS FOR PREPARATION OF (2R)-4-OXO-4-[3-(TRIFLUOROMETHYL)-5,6-DIHYDRO [1,2,4]-TRIAZOLO[4,3-A]PYRAZIN-7(8H)-YL]-L-(2,4,5-TRIFLUOROPHENYL) BUTAN-2-AMINE AND NEW IMPURITIES IN PREPARATION THEREOF

(75) Inventors: Himanshu Madhusudan Kothari, Ahmedabad (IN); Mayank Ghanshyambhai Dave, Ahmedabad (IN); Bipin Pandey, Ahmedabad (IN); Bhavin Shriprasad Shukla, Ahmedabad (IN)

(73) Assignee: Cadila Healthcare Limited, Ahmedabad (IN)

( * ) Notice: Subject to any disclaimer, the term of this patent is extended or adjusted under 35 U.S.C. 154(b) by 31 days.

(21) Appl. No.: 13/060,388

(22) PCT Filed: Aug. 26, 2009

(86) PCT No.: PCT/IN2009/000470
§ 371 (c)(1), (2), (4) Date: May 22, 2011

(87) PCT Pub. No.: WO2010/032264
PCT Pub. Date: Mar. 25, 2010

(65) Prior Publication Data
US 2011/0213149 A1    Sep. 1, 2011

(30) Foreign Application Priority Data

Aug. 27, 2008  (IN) .......................... 1798/MUM/2008
Feb. 2, 2009    (IN) ............................ 188/MUM/2009
Mar. 30, 2009  (IN) ............................ 785/MUM/2009

(51) Int. Cl.
*C07D 417/04* (2006.01)
(52) U.S. Cl.
USPC ...................................................... 544/350
(58) Field of Classification Search
USPC ...................................................... 544/350
See application file for complete search history.

(56) References Cited

U.S. PATENT DOCUMENTS

| | | |
|---|---|---|
| 2003/0100563 A1 | 5/2003 | Edmondson et al. |
| 2004/0167133 A1 | 8/2004 | Edmondson et al. |
| 2005/0032804 A1 | 2/2005 | Cypes et al. |
| 2006/0270679 A1 | 11/2006 | Edmondson et al. |
| 2008/0227786 A1 | 9/2008 | Ferlita et al. |
| 2009/0221592 A1 | 9/2009 | Ellison et al. |
| 2010/0130504 A1 | 5/2010 | Edmondson et al. |
| 2010/0274017 A1* | 10/2010 | Padi et al. ............. 544/350 |

FOREIGN PATENT DOCUMENTS

| | | |
|---|---|---|
| WO | WO03004498 A1 | 1/2003 |
| WO | WO2005003135 A1 | 1/2005 |
| WO | WO2005/020920  * | 3/2005 |
| WO | WO2005020920 A2 | 3/2005 |
| WO | WO2005030127 A2 | 4/2005 |
| WO | WO2005072530 A1 | 8/2005 |
| WO | WO2007035198 A2 | 3/2007 |
| WO | WO2009084024 A2 | 7/2009 |
| WO | WO2009085990 A2 | 7/2009 |

OTHER PUBLICATIONS

European Patent Office, International Preliminary Examining Authority, International Preliminary Report on Patentability (IPRP), PCT/IN2009/000470, Apr. 6, 2011, Munich Germany.
European Patent Office, International Search Report, International Patent Application PCT/IN2009/000470, Mar. 25, 2010.
European Patent Office, Written Opinion, International Patent Application PCT/IN2009/000470, Mar. 25, 2010.
Kim et al; "Triazolopiperazine-amides as dipeptidyl peptidase IV inhibitors: Close analogs of JANUVIA (sitagliptin phosphate)"; Bioorganic & Medicinal Chemistry Letters, Pergamon, Elsevier Science, GB, vol. 17, No. 12, pp. 3373-3377, 2007.

* cited by examiner

*Primary Examiner* — Wu-Cheng Winston Shen
*Assistant Examiner* — Karen Cheng
(74) *Attorney, Agent, or Firm* — IpHorgan Ltd.

(57) ABSTRACT

The present invention relates to synthesis of β-amino acid derivatives of formula (I) and its salts of formula (Ia) by a novel process. The process comprises the reduction of a protected or unprotected prochiral β-amino acrylic acid or derivative there of, by using borane containing reducing agents at atmospheric pressure. The resulting racemic β-amino compound is resolved to a pure stereoisomer of formula (I), specifically to (2R)-4-oxo-4-[3-Ctrifluoromethyl)-5,6-dihydrol[1,2,4]triazolo[4,3-a]pyrazin-7(8H)-yl]-1-(2,4,4-trifluorophenyl)butan-2-amine. In an embodiment the invention disclosed polymorphic forms of formula (I), phosphate salt of formula (I) and also a Dibenzoyl-L-tartaric acid salt of formula (I).

8 Claims, 6 Drawing Sheets

PROCESS FOR PREPARATION OF (2R)-4-OXO-4-[3-(TRIFLUOROMETHYL)-5,6-DIHYDRO [1,2,4]-TRIAZOLO[4,3-A]PYRAZIN-7(8H)-YL]-L-(2,4,5-TRIFLUOROPHENYL) BUTAN-2-AMINE AND NEW IMPURITIES IN PREPARATION THEREOF

Priority is claimed to provisional application No. 1798/MUM/2008, filed on Aug. 27, 2008, provisional application No. 188/MUM/2009, filed on Feb. 2, 2009 and provisional application No. 785/MUM/2009, filed on Mar. 30, 2009.

BACKGROUND OF THE INVENTION

The compound of formula (I) is a an industrially useful compound having the chemical name (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine and the following structure.

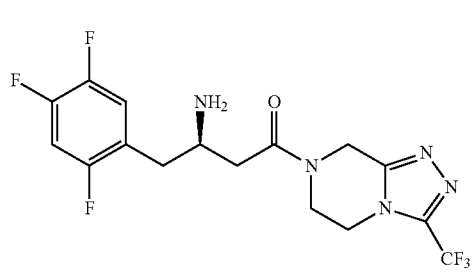

(I)

WO 03004498 and U.S. Pat. No. 6,699,871 both assigned to Merck & Co., describes a class of beta-amino tetrahydro-triazolo[4,3-a]pyrazines, which are inhibitors of DPP-IV. Disclosed therein are compounds, whose general formula is,

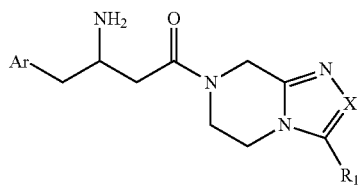

Specifically disclosed in WO 03004498 is (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine. A specific method for producing Sitagliptin or a salt thereof is disclosed here, depicted by following scheme,

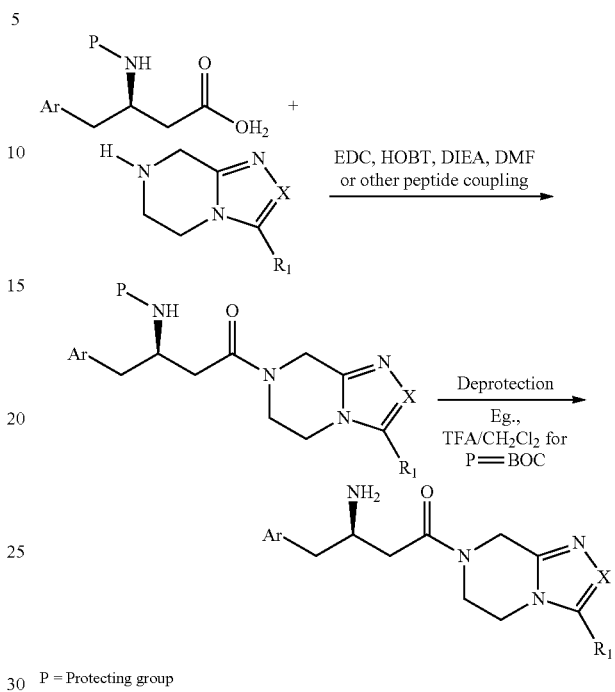

P = Protecting group

However here the overall chemical and optical yield reported is low and there is no mention of stereoisomeric yield.

Another process for preparation of compound of formula (I) is disclosed in WO 2004087650 which involves the formation of chiral benzyloxyazetidinone intermediate, which later on suitable coupling gives the final product. In this process, chiral reagents have been used from the beginning.

WO 2004085661 describes another process for preparation of chiral beta amino acid derivatives including compound of formula (I). Here S-phenylglycine amide (S-PGA) as a chiral auxiliary is used to get pure Z-enamines from diketone. Here a metal catalyst like $PtO_2$ is used, which is expensive and high pressure is required. Here >90% e.e is reported for the reduced amine.

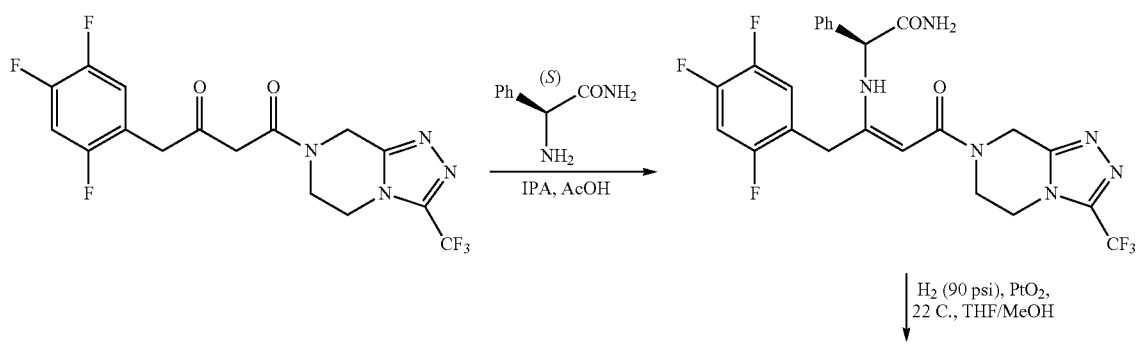

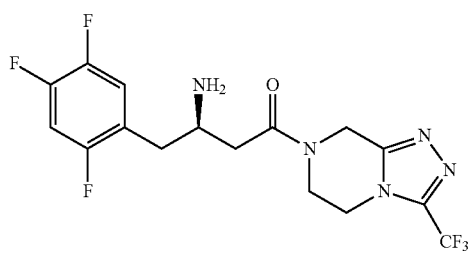
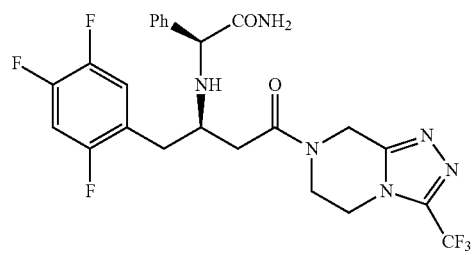

WO 2004085378 and WO 2006081151 describe a process of preparation of chiral beta amino acid derivatives which includes compound of formula (I). The product is prepared by an enantioselective reduction via transition metal catalyzed asymmetric hydrogenation at high pressure of a prochiral enamine. In WO 2004085378, hydrogenation of enamine is carried out to get final product using a very special catalyst e.g. R,S t-butyl Josiphos, as given below, and another special catalyst is used in WO 2006081151 as given below,

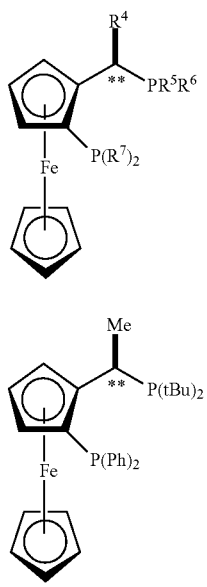

The chiral purity of the product after reduction is claimed to be >70% e.e. The scheme is depicted below:

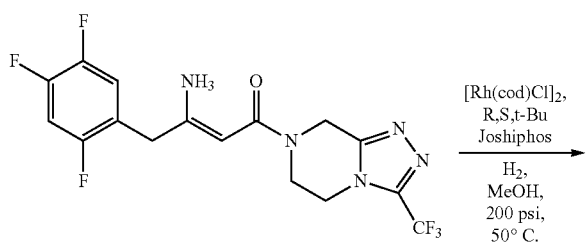

WO 2005097733 describes a process of preparation of compound of formula (I) by asymmetric hydrogenation using Rhodium metal precursor complexes with chiral mono or bis phosphine ligand. Such mono and bis phosphine ligand disclosed are depicted below:

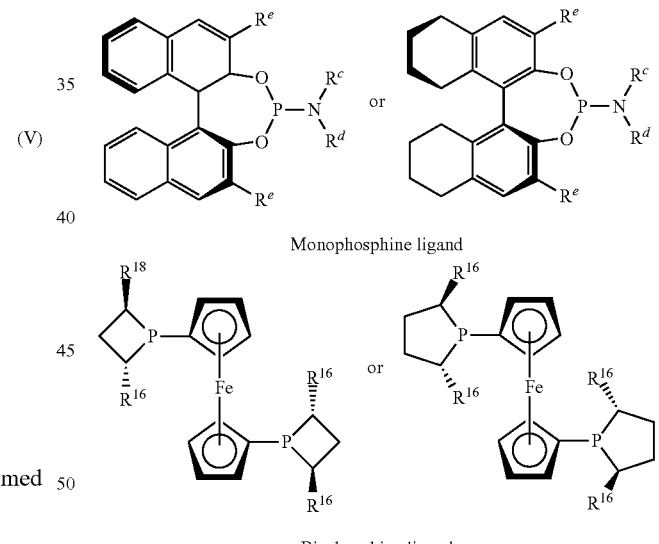

But in all the above processes, the chiral metal catalysts and the diastereoselective catalysts used are very difficult to prepare and are very expensive. The conditions in which the reactions are carried out are extreme i.e. at high pressure, high temperature, etc. Hence there is a need in the art to develop a simple and efficient process for the bulk production of compound of formula (I).

WO2009070314 discloses process for the preparation of crystalline form I of compound of formula (I), comprising combining a salt of compound of formula (I), water and inorganic base to obtain crystalline form I.

Resolution of an amine to get chiral enantiomer is well known. Even in U.S. Pat. No. 6,699,871, col. 5 and 6 describes the possibility of resolution to get the R-isomer of formula I. The real challenge for a process chemist in resolution is to identify the right resolving agent, solvents, reaction conditions, additives and molar ratio of reagents which can give maximum chirally pure enantiomer in least number of unit operations.

WO2009084024 discloses process for the preparation of compound of formula (I) and its pharmaceutically acceptable salts by resolving the amine with a resolving agent. However the identity of resolving agent is not clear. Most of the time the patent application describe the resolving agent as dibenzyl-L-tartarte salts of formula (I), where as Example 5a and 5c described the use of (−)-dibenzolyl-L-tartaric acid. Surprisingly, claim no-3 discloses the resolving agent (−)-dibenzoyl-L-tartaric acid. Subsequently, claim no. 17 claim dibenzyl-L-tartaric acid diastereomer of formula (I).

Naturally for a person skilled in the art, it is not clear which is the actual resolving agent. Additionally, the same document also describes a resolution of a racemic (50:50 mixture of R & S) amine with a chirally pure resolving agent which gives dibenzolyl-L-tartaric acid diastereomer of formula (I) having ratio of (R) and (S) isomers 50:50 (racemic mixture). Of course, by subsequent solvent treatments the desired diastereomer is obtained by repeated recrystallization to get a chiral purity 85-90%. (Example-5a, 5b and 5c)

People skilled in the art of polymorphism know it very well that the XRD pattern of the compound change by variation in the degree of purity or impurity of the compound. However the document disclosed the XRD and DSC of diastereomer of formula I, having 10-15% of chiral impurity. (Example-5a, 5b and 5c).

The same document also discloses the DSC of 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine, which shows only one peak indicating the presence of a single isomer of 4-oxo-4-[3-(trifluoromethyl)-5,6-dihydro[1,2,4] triazolo[4,3-a]pyrazin-7(8H)-yl]-1-(2,4,5-trifluorophenyl) but-2-en-2-amine.

WO2009085990 discloses process for the preparation of compound of formula (I) and its pharmaceutically acceptable salts, wherein after the resolution step, chiral purity of di-p-tolyl-L-tartaric acid salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine is not mentioned. In our hand however, chiral purity of the same compound by using same reagent is only 52.46%.

Process as disclosed in WO2009085990 involves the use of sodium cynoborohydride with methanolic HCl (Example 4) during reduction step which may lead to generation of HCN gas. Naturally, generation of such toxic gases can be difficult to manage at large scale level.

Therefor there is a need for a more definitive, efficient, safe and well-characterized, resolution process with step wise tracking of chiral and chemical purity.

The present invention discloses a process of preparation of compound of formula (I) using simple reagents at normal conditions, giving rise to optimum optical yield and purity in minimum number of steps. We herein also disclose certain new impurities of compound of formula (I), process of preparation of these impurities, which may be used as reference standards.

In order to obtain marketing approval for a new drug product, manufacturers must submit to the regulatory authority evidence that the product is acceptable for administration to humans. Such a submission must include impurity profile of the product to demonstrate that the impurities are either absent, or present in a negligible amount. Different regulatory authorities have promulgated guidelines requiring applicants to identify the impurities present in the product and also disclose their concentration in the product. They also provide the maximum level of impurities allowable in the product. Thus, e.g. USFDA recommends that drug applicants identify all the impurities having concentration of 0.1% or greater than in the active ingredient. Therefore, there is a need to check impurity profile and identify the impurities and also their concentration in the active ingredient.

The product mixture of a reaction rarely is a single compound pure enough to comply with pharmaceutical standards. Side products and byproducts of the reaction and adjunct reagents used in the reaction will, in most cases, be present. At certain stages during processing of the Sitagliptin contained in the product mixture into an active pharmaceutical ingredient, it must be analyzed for purity, typically by HPLC or GC analysis.

Generally, impurities (Side products, byproducts and adjunct reagents) are identified spectroscopically and by other physical methods and then the impurities are associated with a peak position in a chromatogram. Thereafter, the impurity can be identified by its position in the chromatogram, which is conventionally measured in minutes between injection of the sample on the column and elution of the particular component through the detector, known as "retention time". This time period varies daily based upon the condition of the instrumentation and many other factors. To mitigate the effect that such variations have upon accurate identification of an impurity, practitioners use "relative retention time" (RRT) to identified impurities. The RRT of an impurity is its retention time divided by the retention time of some reference marker. Thus, it is sometimes desirable to select an alternative compound that is added to, or is present in, the mixture in an amount significant enough to be detectable and sufficiently low as not to saturate the column and to use that as the reference marker.

Researchers and developers in drug manufacturing understand that a compound in a relatively pure state can be used as a reference standard" (a "reference marker is similar to a reference standard but it is used for qualitative analysis) to quantify the amount of the compound in an unknown mixture. When the compound is used as an "external standard" a solution of a known concentration of the compound is analyzed by the same technique as the unknown mixture.

The reference standard compound also can be used to quantify the amount of another compound in mixture if the "response factor", which compensates for differences in the sensitivity of the detector to the two compounds, has been predetermined.

The reference standard compound can even be used as an internal standard when the unknown mixture contains some of the reference standard compound by using a technique called "standard addition" wherein at least two samples are prepared by adding known and differing amounts of the internal standard. The proportion of detector response due to the reference standard compound that is originally in the mixture can be determined by extrapolation of a plot of detector response versus the amount of the reference standard compound that was added to each of the sample to zero.

FIELD OF INVENTION

The present invention relates to synthesis of β-amino acid derivatives of formula (I) by a novel process. The compound of formula (I) may be further optionally converted to its salts of formula (Ia). The process comprises the reduction of a protected or unprotected prochiral β-amino acrylic acid or derivative there of, by using borane containing reducing agents at atmospheric pressure. The resulting racemic β-amino compound of formula (VI) is resolved to a pure stereoisomer of formula (I), which can then be converted to compound of formula (Ib). In an embodiment the invention disclosed chiral enrichment of phosphate & other salts of the compound of formula (I).

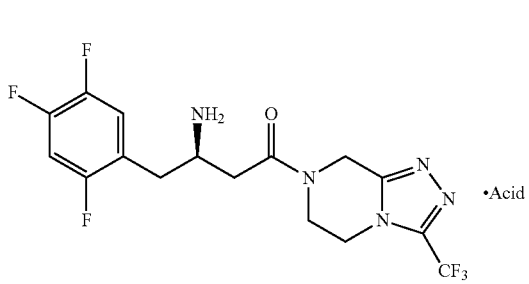

(Ia)

The present invention also discloses a novel compound 3-hydroxy-1-(3-(trifluoromethyl)-5,6-dihydro-[1,2,4]triazolo[4,3-a]pyrazin-7(8H)-yl)-4-(2,4,5-trifluorophenyl)butan-1-one of formula (X) and its salts, as an impurity and process for preparation thereof.

OBJECT OF THE INVENTION

Figure 1:
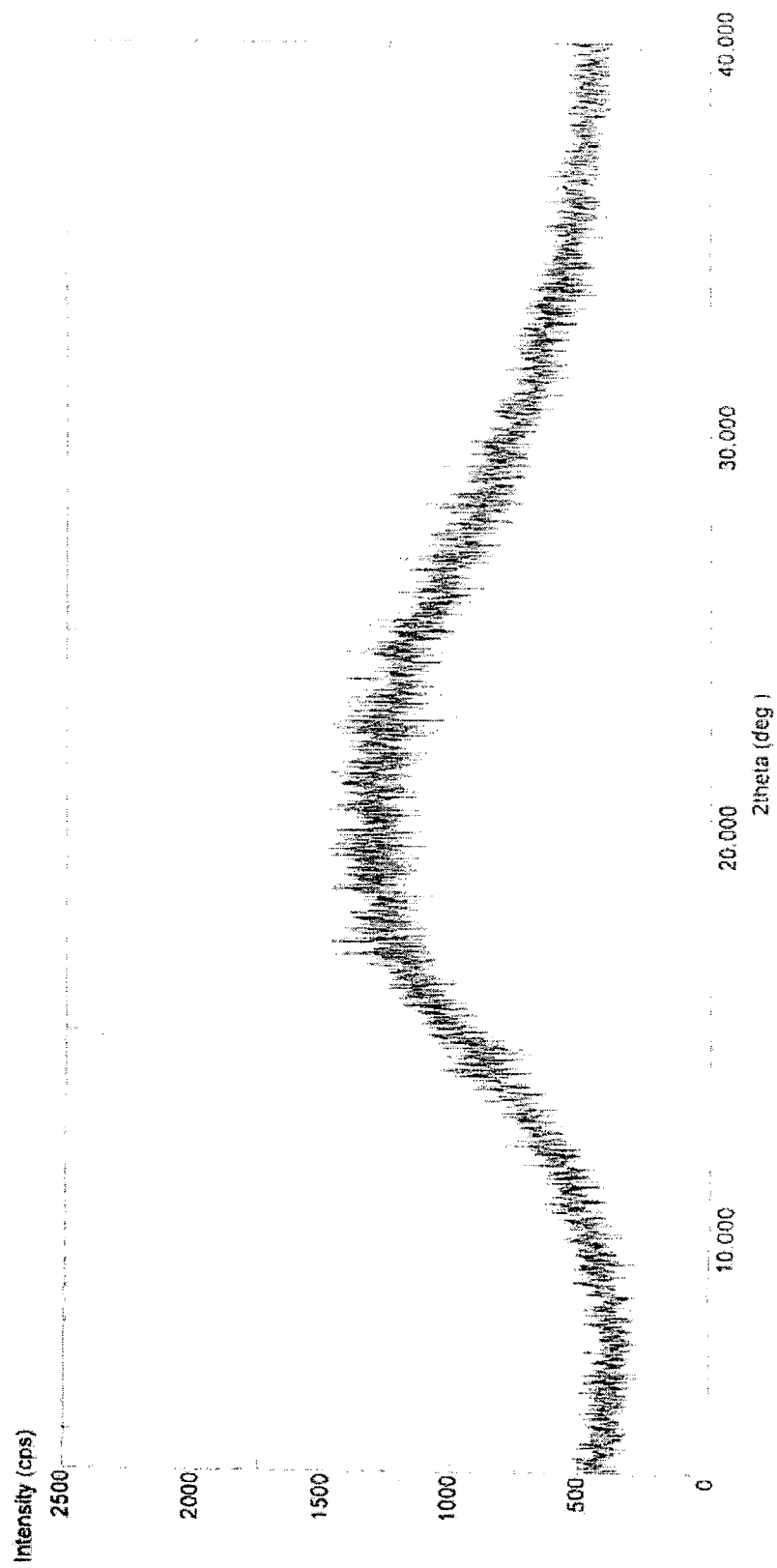
FIG. 1 is a powder X-ray diffraction (XRPD) pattern of amorphous form of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine according to the present invention.

The object of the present invention is to provide an improved process for the preparation of β-amino acid derivatives of formula (I) and its salts of a formula (Ia), as per scheme 1.

In an embodiment is provided a process for preparing racemic β-amino acid derivatives of a formula (VI) by reduction of a protected or unprotected prochiral β-amino acrylic acid (V) or derivative thereof by using borane containing reducing agents.

In an embodiment is provided a crystalline form 3 of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine. In an embodiment is provided a amorphous form of racemic 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine. In an embodiment is provided a novel crystalline form of Dibenzoyl-L-tartarate salt of compound of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine.

In another embodiment is provided a resolution method of racemic β-amino acid derivatives of formula (VI) by using suitable chiral acid resolving agents and optionally in the presence of additives.

In another embodiment is provided a racemization method of enantiomerically enriched unwanted isomer and further, resolution to get β-amino acid derivatives of formula (VI), (wherein R=H) in high purity.

In another embodiment the object of the present invention is to provide a process for the preparation of β-amino acrylic acid or derivative of formula (V) from a metal ion salt of β-Keto compound of formula (IV).

In another embodiment the object of the present invention is to provide a metal ion salt of β-Keto compound of formula (IV) and its process for the preparation and isolation from 2,4,5-trifluorophenyl acetic acid (II).

In further embodiment is provided a process for preparing β-amino acid derivatives of formula (I) in high chemical and chiral purity and which is free from heavy metals.

In a still further embodiment is to provide a process for preparing pharmaceutically acceptable salts of β-amino acid derivatives of formula (I).

In a still further embodiment is provided a novel compound 3-hydroxy-1-(3-(trifluoromethyl)-5,6-dihydro-[1,2,4]triazolo[4,3-a]pyrazin-7(8H)-yl)-4-(2,4,5-trifluorophenyl)butan-1-one of formula (X) and its salts.

In yet another embodiment is provided the use of compound of formula (X) as a reference standard for Sitagliptin.

It has surprisingly been observed that the compound of formula (X) was being formed as an impurity during the process of preparation of compound of formula (I), according to the present invention.

In a still further embodiment is to provide a process for preparing compound of formula (X).

In a still further embodiment is to provide a process for chiral enrichment of pharmaceutically acceptable salts of β-amino acid derivatives of formula (Ib).

DETAILED DESCRIPTION OF THE INVENTION

As used herein, the term "reflux temperature" refers to the boiling point of the solvent.

As used herein, the term "PXRD" refers to powder X-ray diffraction

As used herein, the term "compound of formula (I)" refers to (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine.

As used herein, the term "THF" refers to tetrahydrofuran, the term "DCM" refers to dichloro methane, the term "DMF" refers to dimethyl formamide, the term "DIPE" refers to di-isopropyl ether, the term "MTBE" refers to methyl t-butyl ether, the term "DMSO" refers to dimethyl sulfoxide, the term "DMA" refers to dimethylacetamide, the term "IPA" refers to isopropyl alcohol.

As used herein, the term "DMAP" refers to 4-dimethyl amino pyridine, As used herein, the term "TFA" refers to trifluoro acetic acid, As used herein, the term "NMP" refers to N-methylpyrrolidone, As used herein, the term "N,N-DI-PEA" refers to N,N-diisopropyl ethyl amine.

The compound (1b) represents salts of compound of formula (I) having at least 70% chiral purity;

The compound (1a) represents salts of compound of formula (I) having at least 90% chiral purity.

Scheme-1:

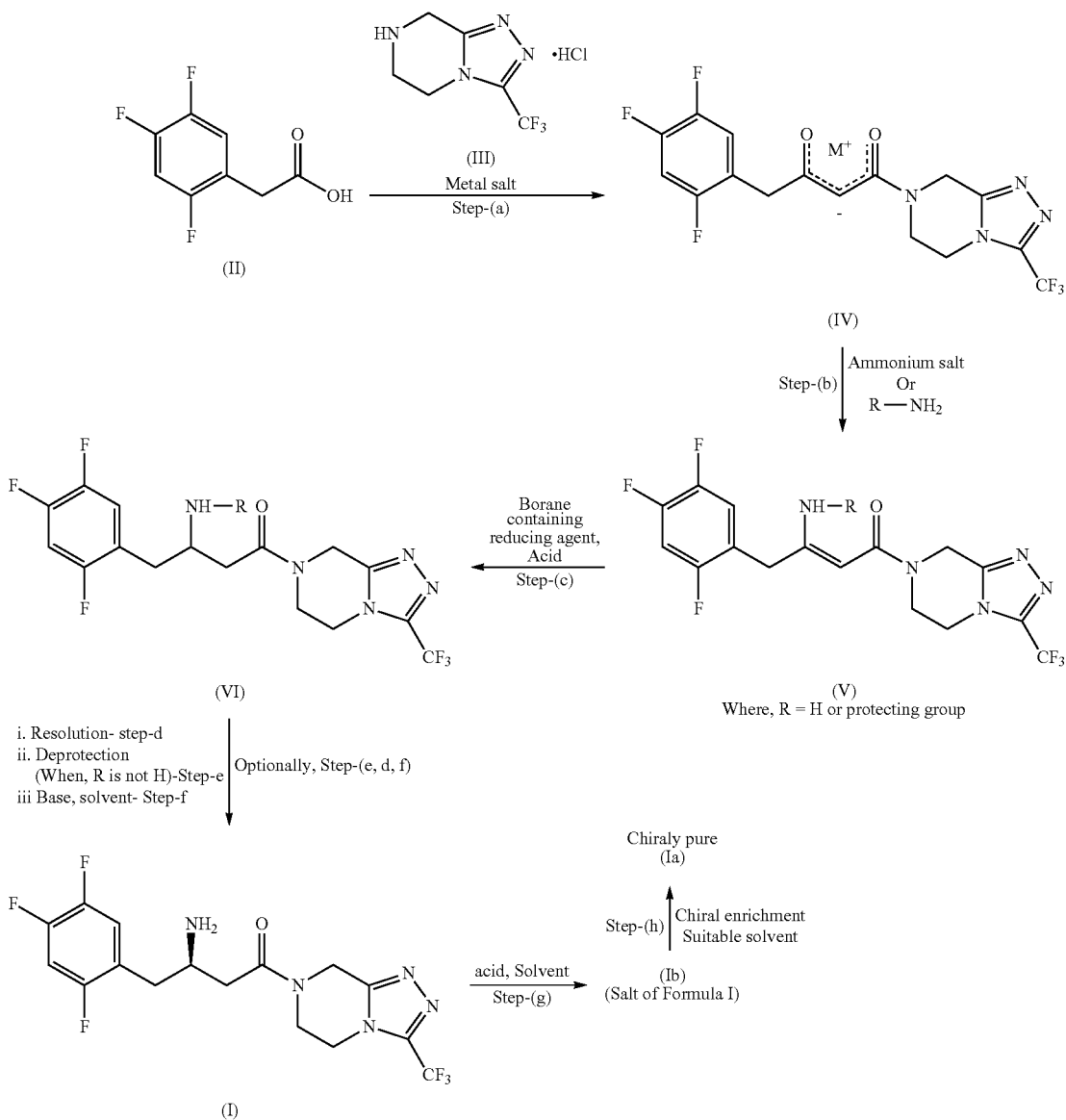

Accordingly, the invention provides an improved process for the preparation of β-amino acid derivatives of formula (I) and its salts of formula (Ia) in high chemical and chiral purity as per scheme 1. The process comprises the steps of, a) Preparation of new metal ion salts of β-Keto acid or its derivative of formula (IV) from trifluorophenylacetic acid (II) or its acid chloride by reacting with Meldrum's acid, 3-trifluoromethyl 5,6,7,8-tetrahydro[1,2,4]triazolo[4,3-a]pyrazine.HCl (III), a suitable base and suitable acid. The stable salt thus obtained is isolated easily as a metal ion salt directly from reaction mixture by adding alkali and alkali earth metal hydroxides, chlorides, carbonate, acetates, sulfates, nitrates and oxides.

b) The metal ion salt of β-Keto acid or its derivative of formula (IV) is reacted with a suitable ammonium salt or with a suitable organic amine in a suitable solvent and optionally in the presence of a suitable acid to get substituted or unsubstituted β-amino acrylic acid or it's derivatives of formula (V).
c) Reducing the β-amino acrylic acid or derivative thereof, of formula (V) by using suitable borane containing reducing agent optionally in the presence of an acid in a suitable solvent at atmospheric pressure provides racemic substituted or unsubstituted β-amino acid derivatives of a formula (VI).
a) Resolution of racemic β-amino acid derivatives of formula (VI) by suitable chiral resolving agents via the formation of the corresponding diastereomeric salt, and optionally in presence of additives in suitable solvent provides diastereomeric salts β-amino acid derivatives of formula (I) in high chemical and chiral purity.
b) Optionally, the deprotection of the protected β-amino acid derivatives of formula (VI) [When, R≠H] by standard techniques reported in the literature yields deprotected β-amino acid derivatives of a formula (VI) [Where, R═H]. Optionally, the deprotection step is carried out before the resolution step.
c) Conversion of diastereomeric salt as obtained in step-(d) or (e) to formula (I) having chiral purity at least 70% ee.
d) Preparation of pharmaceutically acceptable salt of β-amino acid derivatives of a formula (Ib) by reacting with a suitable acid(s) in a suitable solvents.
e) Chiral enrichment of pharmaceutically acceptable salt of β-amino acid derivatives of a formula (Ia) obtained in step-g using suitable solvent.

Step-(a)

In one embodiment, as outlined in step-(a) in above scheme-1, (2,4,5-trifluorophenyl acetic acid) is converted to its acid chloride or to a mixed carboxylic acid carbonic anhydride or to a mixed carboxylic acid anhydride which can be reacted with Meldrum's acid to obtained Meldrum's acid adduct. The Meldrum's acid adduct is reacted optionally in situ with 3-trifluoromethyl-5,6,7,8-tetrahydro[1,2,4]triazolo[4,3-a]pyrazine.HCl salt in the presence of an acid such as HCl, HBr, $H_2SO_4$, $H_3PO_4$, PPA, trichloroacetic acid, trifluoroacetic acid, $CH_3SO_3H$, $CF_3SO_3H$, p-TSA, benzenesulfonic acid, camphorsulfonic acid, acetic acid, formic acid, pivalic acid and like; in a suitable organic solvent, which on treatment with suitable metal salts give salt of formula (IV) as solid which is isolated.

To prepare acid chloride of 2,4,5-trifluorophenyl acetic acid, reagents used may be selected from thionyl chloride, oxalyl chloride, $PCl_5$ and like. The reaction is carried out in a suitable solvent at 0° C. to a reflux temperature of the solvent used and optionally in presence of a base. To prepare a mixed carboxylic acid anhydride and a mixed carboxylic acid carbonic anhydride of 2,4,5-trifluorophenyl acetic acid, reagent used may be selected from pivaloyl chloride and di-2-pyridyl carbonate, isobutyl chloroformate and like.

The suitable solvents used in step-(a) may be selected from ethers such as THF, DIPE, 2-methyl tetrahydrofuran; esters like ethyl acetate, isopropyl acetate; hydrocarbons such as toluene; halogenated hydrocarbons such as DCM; DMF, DMSO, DMAc, NMP, acetonitrile and mixtures thereof.

The suitable base used in step-(a) may be selected from triethyl amine, diisopropyl ethyl amine, dimethylamino pyridine, DMF, collidine, imidazole, pyridine, N,N-dimethyl aniline and like.

The reaction is carried out at temperature ranging from at 0° C. to reflux temperature of the solvent used.

The product of formula (IV) was isolated as a solid metal ion salts of Na, K, Li, Ca, Mg, Cu, Cs by using suitable reagents may be selected from Na, K, Li, Ca, Mg, Cu may be hydroxides of Na, K, Li, metal chlorides of Ca, Mg, Cu, Cs metal acetates of Ca, Mg, Cu, metal sulfates of Ca, Mg, Cu, metal nitrates of Ca, Mg, Cu and suitable metal oxides.

The product of formula (IV) was isolated as solid metal ion salts, the process of isolation comprises:

After completion of the reaction the aqueous solution of alkali metal ion salts was added such as alkali metal hydroxide, alkali metal carbonate till pH>9 to 10. Further, it may be converted to alkali earth metal salts such as Ca, Cu and Mg salts of formula (IV) by adding metal chlorides of Ca, Mg, Cu, Cs; metal acetates of Ca, Mg, Cu, Cs; metal sulfates of Ca, Mg, Cu, Cs; metal nitrates of Ca, Mg, Cu and suitable metal oxides into the solution of alkali metal salts.

Optionally, the isolated alkali metal salt of formula (IV) may be further converted to Ca, Cu and Mg salts of formula (IV) by adding metal chlorides of Ca, Mg, Cu, Cs; metal acetates of Ca, Mg, Cu, Cs; metal sulfates of Ca, Mg, Cu, Cs; metal nitrates of Ca, Mg, Cu, Cs and suitable metal oxides into the solution of alkali metal salts in a suitable solvents. It has additionally been found according to the invention that the metal salts of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one) (IV) may further contain 2-10% water by weight, preferably, 4-6% water by weight.

Here, the metal salt of formula (IV) was obtained in very high yield, easy to isolate on large scale and stable.

Step-(b)

In one embodiment, as outlined in step-(b) in above scheme-1, the metal salt of formula (IV) thus obtained was reacted with a suitable ammonium source or with a suitable organic amine in a suitable solvent and optionally in the presence of a suitable acid to get substituted or unsubstituted β-amino acrylic acid or it's derivatives of formula (V) (Wherein R═H or a suitable protecting group).

In step (b) the suitable ammonium source used may be selected from ammonium acetate, ammonium carbonate, ammonium hydroxide, ammonium formate, ammonium lactate, ammonium citrate dibasic, ammonium carbamate, ammonium benzoate and the like.

The suitable organic amines used for obtaining the protected enamine compounds of formula (V) (Wherein R=suitable protecting group) in step (b) may be selected from benzylamine, α-methylphenethyl amine & the like.

Suitable protecting group which may be used may be selected from those disclosed in Text book-Title: Protective Groups in Organic Synthesis, 3$^{rd}$ Edition, John Wiley & Sons, By-T. W. Grene and Peter G. M. Wuts).

The suitable solvents used in step-(b) may be selected from suitable alcohols like methanol, ethanol, isopropanol, butanol, 1,2-dimethoxy ethanol, 2-methoxy ethanol, 2-ethoxy ethanol; ethers like 1,4-dioxane, THF; esters like ethyl acetate and isopropyl acetate; water and their suitable mixtures.

The reaction was carried out at temperature ranging from room temperature to reflux temperature of the particular solvent used.

The suitable acids used in step-(b) may be selected from suitable inorganic acid such as HCl, HBr, $H_2SO_4$ and phosphoric acid and the like or suitable organic acid which may be selected from acetic acid, formic acid, p-toluene sulfonic acid and the like.

Here, the DSC of 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine, which shows two peaks indicates presence of two isomer (i.e: E/Z isomers) of the 4-oxo- 4-[3-(trifluoromethyl)-5,6-dihydro[1,2,4]triazolo[4,3-a] pyrazin-7(8H)-yl]-1-(2,4,5-trifluorophenyl)but-2-en-2-amine.

Step-(c)

In one embodiment, as outlined in step-(c) in above scheme-1, substituted or unsubstituted β-amino acrylic acid or its derivative of formula (V) (Wherein R=H or suitable protecting group) is reduced to obtain substituted or unsubstituted β-amino acid derivatives of formula (VI) (Wherein R=H or suitable protecting group) by using borane containing reducing agents.

The suitable borane containing reducing agents used in step-(c) may be selected from borohydride reducing agents such as, $NaBH_4$, $NaCNBH_4$, $Na(OAc)_3BH$, $LiBH_4$, $KBH_4$, $Na(OMe)_3BH$, $K(OiPr)_3BH$, 9-borabicyclo[3.3.1]nonane (9-BBN), (R) or (S)—B-isopinocampheyl-9-borabicyclo[3,3,1]nonane; $BH_3$ complexes such as, $BH_3$-ammonia, $BH_3$-t-Bu amine, $BH_3$-triethylamine, $BH_3$-trimethylamine, $BH_3$-pyridine, $BH_3$-pyrrole, $BH_3$-piperazine, $BH_3$-piperidine; borane ether complex such as $BH_3$-THF; borane phosphine complexes such as $BH_3$-triphenylphosphine complex; borane sulfide complexes such as borane methylsulfide complex, borane 1,4-oxathiane.

Above disclosed borane containing reducing agents is first reacted with a suitable acid selected from, inorganic acids such as HCl, $H_2SO_4$ & the like; organic acids selected from lower alkyl acid such as $CH_3COOH$, $CH_3CH_2COOH$; lower haloalkyl acid such as $CF_3COOH$, dichloroacetic acid; phenyl or substituted phenyl acid such as benzoic acid; loweralkyl sulfonic acid such as $CH_3SO_3H$, $C_2H_5SO_3H$; haloalkyl sulfonic acid such as $CF_3SO_3H$; phenyl sulfonic acid such as $C_6H_5SO_3H$; loweralkyl substituted phenyl sulfonic acid or naphthyl sulfonic acid; phosophoric acid, lower alkyl phosphonic acid such as methylphosphonic acid, phenylphosphonic acid, $BF_3.OEt_2$, tartaric acid, modified tartaric acid, camphorsulfonic acid and the like.

The suitable solvents used in step-(c) may be selected suitable alcohols like methanol, ethanol, isopropanol, butanol, 1,2-dimethoxy ethanol, 2-methoxy ethanol, 2-ethoxy ethanol and ethylene glycol; ethers like diethyl ether, 1,4-dioxane, dimethoxy ethane, DIPE, MTBE, THF, 2-methyl tetrahydrofuran; aprotic polar solvents such as DMF, DMSO, DMA and their suitable mixtures.

The reaction was carried out at −80 to 50° C.

Alternatively, reduction can be done by adding suitable reducing agent(s) as above, to a solution of the substituted or unsubstituted β-amino acrylic acid or its derivative of formula (V) (Wherein R=H or suitable protecting group), followed by addition of the an acid in a suitable solvent(s) at −80 to 50° C. Substituted or unsubstituted β-amino acid derivatives of formula (VI) (Wherein R=H or suitable protecting group) may be obtained as a racemic mixture.

The molar ratio of substituted or unsubstituted β-amino acrylic acid or its derivative of formula (V) (Wherein R=H or suitable protecting group), borane containing reducing agent and acid is 1:1 to 10:1 to 20. Preferably the molar ratio used is 1:2 to 4:4 to 10.

In one preferred embodiment of the invention is disclosed in amorphous form of compound of formula (VI) (Wherein R=H).

In a still further preferred embodiment, the racemic base of formula (VI) (Wherein R=H) contains 0.1-10% water by weight, preferably, 4-6% water by weight.

Amorphous form of formula (VI) (Wherein R=H) obtained according to the process of the present invention is characterized by an XPRD pattern substantially in accordance with the pattern as in FIG. 1.

The complete x-ray powder spectrum, which was recorded with a Rigaku multifelx 2.0 Kilowatt X-ray powder diffractometer model using copper radiation. The X-ray diffraction pattern was recorded by keeping the instrument parameters listed below:

i) X-ray: Cu/40 kv/30 mA, Diverging slit: 1°, Scattering slit: 1°, Receiving slit: 0.15 mm, Monochromator RS: 0.8 mm, Counter: Scintillation counters;

Scan mode: Continuous, Scan speed: $4.000^{deg.}$/min., Sampling width: 0.010°, Scan axes: 2 theta vs CPS, Scan range: 4° to 40.0°, Theta offset: 0.000.

ii) Differential scanning calorimetric analysis was carried out in a DSC-60 model from Shimadzu (S/W: TA-60WS Aquisition version 2.1.0.0) by keeping following parameters, Sample Size: Approx. 1-2 mg, Sample Pans: Hermetic/Crimping Pans, Start Temperature: 50° C., End Temperature: 300° C., Rate of Heating: 10° C./min., Purge Gas: Nitrogen, Flowrate: 20 ml/min iii) The infrared (IR) spectrum has been recorded on a Shimadzu FTIR-8400 model spectrophotometer, between 450 $cm^{-1}$ and 4000 $cm^{-1}$, with a resolution of 4 $cm^{-1}$ in a KBr pellet.

iv) (2R)-4-oxo-4-[3-(trifluoromethyl)-5,6-dihydro[1,2,4]-triazolo[4,3-a]pyrazin-7(8H)-yl]-1-(2,4,5-trifluorophenyl)-butan-2-amine and its salts were analyzed for purity by analytical HPLC at λmax 210 nm using column YMC-C8, 250 mm×4.6 mm×4 mm or its equivalent on AGILENT 1100 series under the following conditions, Detector: UV absorption photometer Wave length: 210 nm
Column temp.: 25° C.
Flow rate: 1.0 mL/min. Injection Vol.: 10 μL
Mobile Phase: 10 mM $KH_2PO_4$ (pH-6.8): Acetonitrile (55:45)

(2R)-4-oxo-4-[3-(trifluoromethyl)-5,6-dihydro[1,2,4]-triazolo[4,3-a]pyrazin-7(8H)-yl]-1-(2,4,5-trifluorophenyl) butan-2-amine and its salts were analyzed for chiral purity by HPLC at λmax 268 nm using column Chiral-Cel OJ-H, 250 mm×4.6 mm×5μ or its equivalent on Shimadzu LCVP model under the following conditions, Detector: UV absorption photometer Wave length: 268 nm
Column temp.: 35° C.
Flow rate: 0.8 mL/min. Injection Vol.: 10 μL
Mobile Phase: 0.1% diethyl amine in [n-Hexane:Ethanol (90:10)]

v) Melting points were taken on VEEGO make model VMP-D melting point apparatus and are uncorrected Step-(d)

In one embodiment, as outlined in step-(d) in above scheme-1, resolution of racemic O-amino acid derivatives of formula (VI) (Wherein, R=H or suitable protecting groups) by a suitable enantiomerically pure acid resolving agent(s) and optionally in presence of additive like suitable inorganic acid or suitable organic acid such as formic acid, acetic acid and water, in suitable solvents to obtain diastereoisomeric salts substituted or unsubstituted β-amino acid derivatives of a formula (I) with high chemical and chiral purity.

Suitable chiral acids used in step-(d) may be selected from tartaric acid, di-p-toluoyl tartaric acid, dibenzoyltartaric acid, o-nitrobenzoyl tartaric acid, lactic acid, 10-camphorsulfonic acid, 8-camphorsulfonic acid, malic acid, N-acetyl glutamic acid, mandelic acid, o-acetylmandelic acid, o-methylmandelic acid, thiazolidine-4-carboxylic acid, α-methoxyphenylacetic acid, α-methoxy-α-trifluoromethylphenylacetic acid, 2-pyrrrolidone-5-carboxylic acid and the like. Preferably the chiral acid used for resolution may be selected from tartaric acid and dibenzoyltartaric acid.

The suitable solvents used in step-(d) may be selected from suitable alcohols like methanol, ethanol, isopropanol, butanol, 1,2-dimethoxy ethanol, 2-methoxy ethanol, 2-ethoxy ethanol, isoamyl alcohol and ethylene glycol; esters like ethyl acetate and isopropyl acetate; chlorinated solvents like chloroform and dichloromethane; nitriles like acetonitrile; hydrocarbons like toluene, xylene and chlorobenzene; ketones like acetone, methyl ethyl ketone; ethers like diethyl ether, 1,4-dioxane, DIPE, MTBE, THF; aprotic polar solvents such as DMF, DMSO, DMA; water and their suitable mixtures.

The molar ratio of β-amino acid derivatives of formula (VI) (Wherein, R=H or suitable protecting groups) and resolving agent is preferably in the range of 1:0.5 to 1.5.

In one of the preferred embodiment of the present invention the diastereoisomeric salt of the formula (VI) (Wherein, R=H or suitable protecting groups) was prepared by adding chiral acid either as a solid to a solution of compound formula (VI) (Wherein, R=H or suitable protecting groups), or after dissolving the acid in a suitable solvent to form a mixture and adding compound formula (VI) (Wherein, R=H or suitable protecting groups) in a suitable solvent, at −10° C. to reflux temperature of the solvent used. It is stirred or kept for a period of time as required for complete salt formation. The exact time required for complete salt formation can be readily determined by a person skilled in the art. The salt is filtered and washed with a suitable solvent.

The diastereoisomeric salts are purified using suitable solvents selected from but not limited to a suitable alcohols like methanol, ethanol, isopropanol, butanol, 1,2-dimethoxy ethanol, 2-methoxy ethanol, 2-ethoxy ethanol, isoamyl alcohol and ethylene glycol; esters like ethyl acetate and isopropyl acetate; chlorinated solvents like chloroform and dichloromethane; nitriles like acetonitrile; hydrocarbons like toluene, xylene and chlorobenzene; ketones like acetone, methyl ethyl ketone; ethers like diethyl ether, 1,4-dioxane, DIPE, MTBE, THF; aprotic polar solvents such as DMF, DMSO, DMA; water and their suitable mixtures.

In one of the preferred embodiment of the present invention is disclosed the L-tartarate salt of compound of formula (I) (wherein, R=H) and process for the preparation thereof. The process involves adding L-tartaric acid either as a solid to a solution of racemic base of formula (VI) as obtained in step-(c) or after dissolving the acid in a suitable solvent to form a mixture and adding racemic base of formula (VI) in a suitable solvent, at −10° C. to reflux temperature of the solvent used. It is stirred or kept for a period of time as required for a more complete salt formation. The exact time required for complete salt formation can be readily determined by a person skilled in the art. The salt is filtered and washed with a suitable solvent.

It has been found that, by such process, L-tartarate salt of compound of formula (I) (wherein, R=H) can be made having the chiral purity>92% and which further contains 2-10% water by weight, preferably, 4-6% water by weight.

In one of the preferred embodiment invention is disclosed the L-tartarate salt of compound of formula (I) (wherein, R=H) which was subsequently converted to obtain base of formula (I) having chiral purity>92%.

The invention thus describes the Dibenzoyl-L-tartarate salt of compound of formula (I) (R=H) and its use to prepare base of formula (I) having chiral purity 70%.

Figure 2:
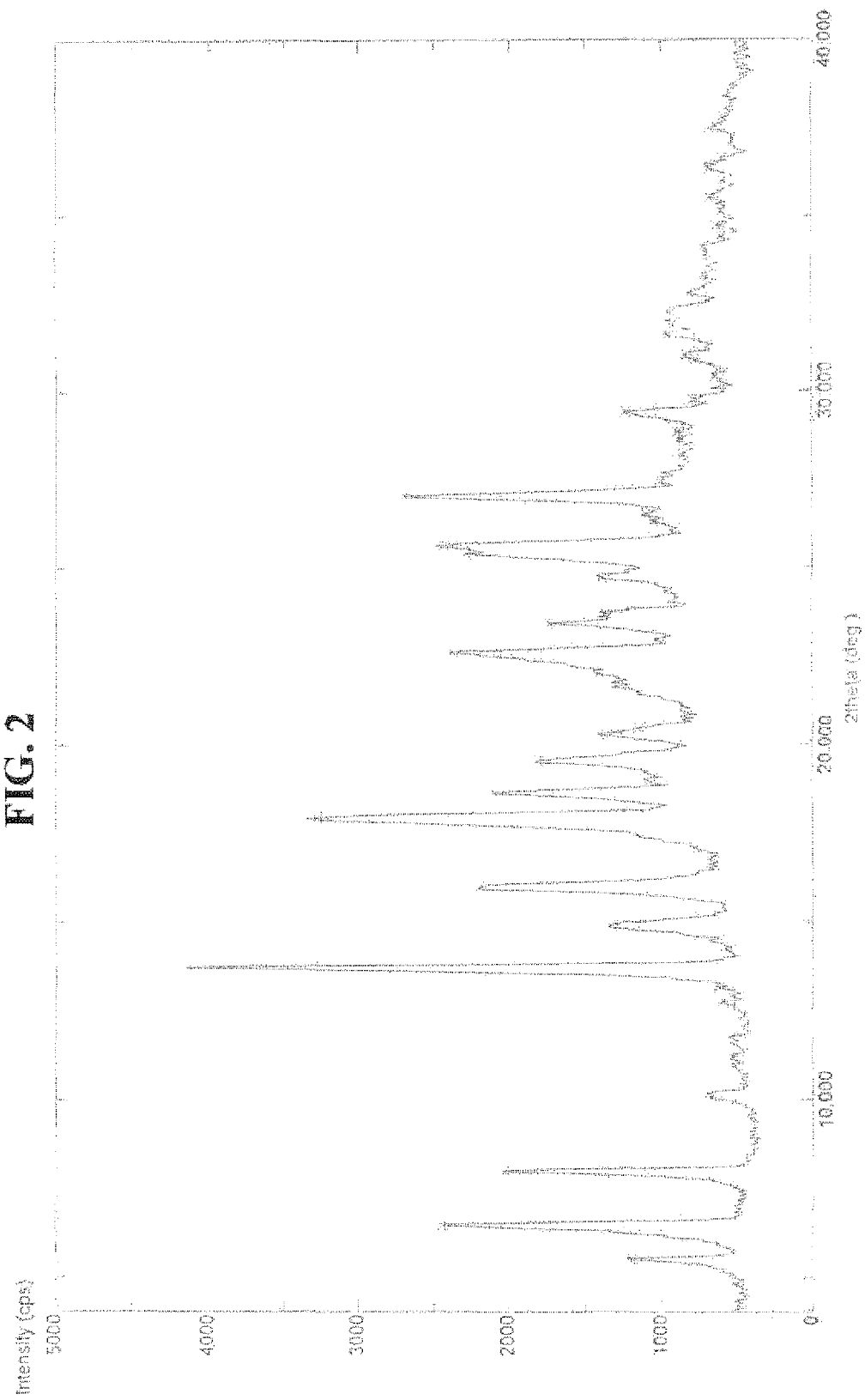
FIG. 2 is a powder X-ray diffraction (XRPD) pattern of Dibenzoyl-L-tartarate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine according to the present invention

Dibenzoyl-L-tartarate salt of compound of formula (I) (R=H) obtained according to the process of the present invention is characterized by an XPRD pattern substantially in accordance with the pattern FIG. 2.

It is also characterized by an XPRD peaks at about 6.48, 7.98, 13.73, 15.98, 17.95, 22.59, 25.39°±0.2 degrees 2θ. The crystalline form further characterized by an additional XPRD peaks at about 5.50, 14.87, 18.66, 19.54, 20.28, 23.39, 25.65°±0.2° degrees 2θ.

It has surprisingly been found according to the invention that, diastereomeric salt of compound of formula (I) (wherein, R=H or protecting group) is at least partly crystalline or completely crystalline or amorphous form which is characterized by PXRD peaks.

Step-(e)

Optionally, deprotection of the protected β-amino acid derivatives of a formula (VI) [When, R≠H] by standard techniques reported in the literature provides deprotected β-amino acid derivatives of formula (VI) [Where, R≠H]. (See for e.g. Protection and Deprotection of amines in Text book-Title: Protective Groups in Organic Synthesis, 3$^{rd}$ Edition, John Wiley & Sons, By-T. W. Grene and Peter G. M. Wuts).

Optionally, deprotection is carried out before the resolution step.

Step-(f)

In a further embodiment of the invention the diastereoisomeric salt obtained in step-(d) or (e) are converted to the compound of formula (I) with high chiral purity as outlined in step-(f) of scheme-1 above. The process involves dissolving the diastereoisomeric salt in a suitable solvent & then basifying it using suitable aqueous solution of base. The free base of the product is extracted in suitable organic solvent. The organic solvent was separated. After water washings and drying, solvent is evaporated to obtained compound of formula (I) with chiral purity≧70% and chemical purity≧95%.

Stirring time and volume of the solvent can be readily determined by a person skilled in the art and will also depend on parameters such as solubility of the desired and unwanted stereoisomers of the salt.

A suitable solvent used in step-(f) is selected from but not limited to alcohols such as t-butanol; ketones such as MIBK; esters such as ethyl acetate, iso-propyl acetate and the like, hydrocarbons such as toluene, xylene and the like, ethers such as THF and the like, halogenated solvents such as chloroform, dichloromethane and the like or their suitable mixtures.

A suitable base used in step-(f) is selected from suitable hydroxides such as NaOH, KOH, LiOH and like, suitable carbonates such as $NaHCO_3$, $Na_2CO_3$, $K_2CO_3$ and like.

Figure 3:
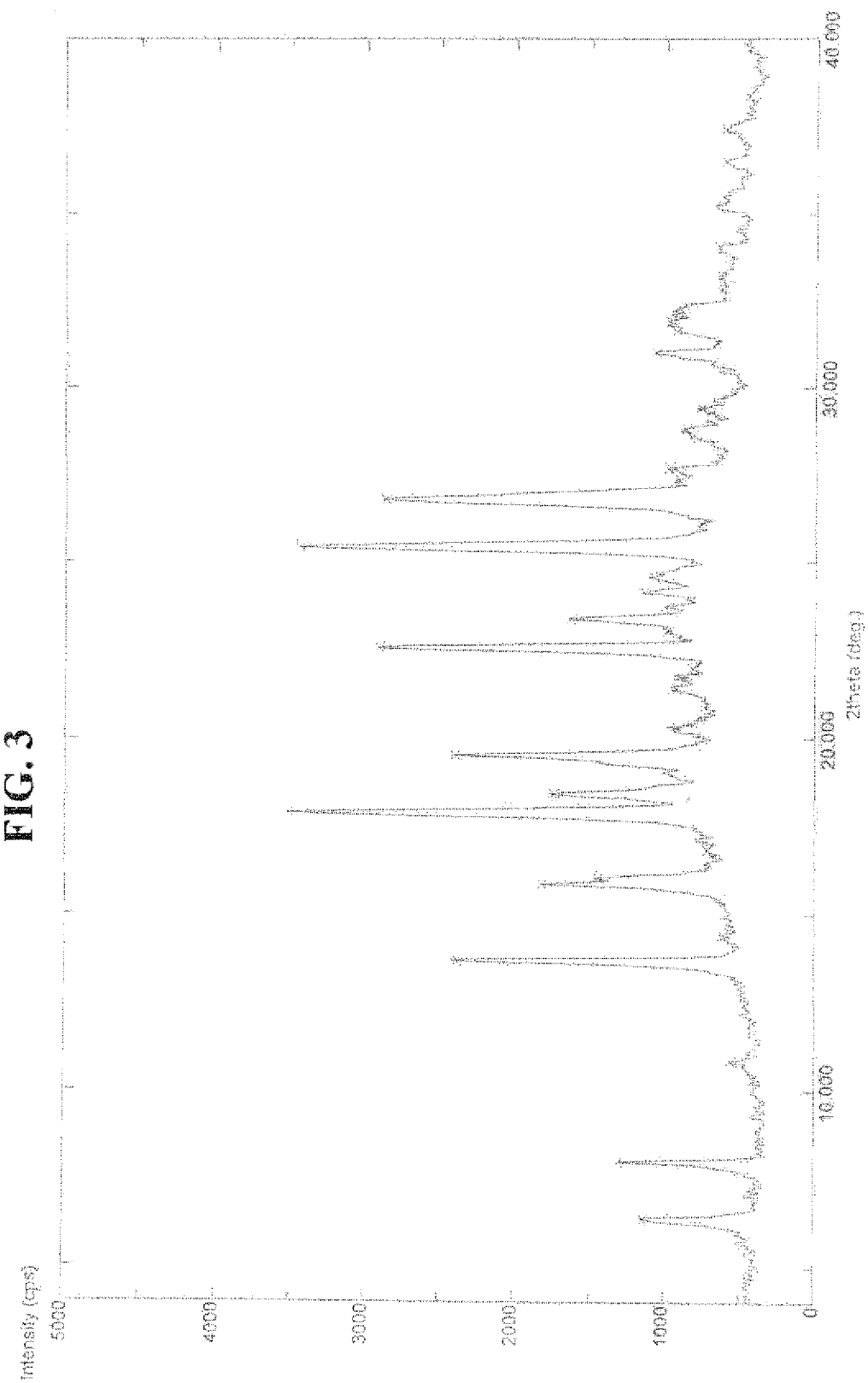
FIG. 3 is a powder X-ray diffraction (XRPD) pattern of the crystalline form 3 of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine according to the present invention.
Figure 4:
FIG. 4 is a Differential scanning calorimetry of crystalline form 3 of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine according to the present invention.

In a further embodiment of the invention disclosed a crystalline Form 3 of the (2R)4-oxo-4-[3-(trifluoromethyl)-5,6-dihydro[1,2,4]triazolo[4,3-a]pyrazin-7(8H)-yl]-1-(2,4,5-trifluorophenyl)butan-2-amine, which has at least one of the following characteristics:

f) a powder X-ray diffraction pattern substantially in accordance with FIG. 3;

ii) a powder X-ray diffraction pattern having peaks at about 6.38, 8.00, 13.72, 17.91, 22.54, 25.44, 26.81±0.2 degrees 2-theta;

iii) a powder X-ray diffraction pattern having additional peaks at about 15.86, 16.05, 18.44, 19.44 and 23.36±0.2 degrees 2-theta Crystalline form 3 of (2R) 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine characterized by a DSC comprising endothermic peaks at about 88° C.±2° C. and about 101° C.±2° C.

Step-(g)

The chirally pure compound of formula (I) thus obtained, is converted to its corresponding acid addition salts of formula (Ib) by reacting with corresponding acids in suitable solvents as outlined in step (g) of Scheme 1.

The suitable solvents used in step-(g) may be selected from alcohols such as methanol, ethanol, isopropanol, butanol, 1,2-dimethoxy ethanol, 2-methoxy ethanol, 2-ethoxy ethanol, ethylene glycol and the like; hydrocarbons such as hexane, cyclohexane, toluene, chloro benzene and like; esters such as ethyl acetate, isopropyl acetate & the like; nitriles such as acetonitrile & the like; ethers such as, DIPE, 1,4-dioxane, THF & the like; ketones such as acetone, MIBK and like; aprotic polar solvents such as DMF, DMSO, DMA & the like; water and suitable mixtures of one or more of the solvents described above.

The suitable acid used in step-(g) may be selected from phosphoric acid, HCl, benzenesulfonic acid, p-toluenesulfonic acid, 10-camphorsulfonic acid, tartaric acid, dodecylsulfuric acid, citric acid, maleic acid, fumaric acid and the like.

In a preferred embodiment, the phosphate salt of the compound of formula (I), having chiral purity of at least ≧95% is prepared according to the present invention.

Figure 5:
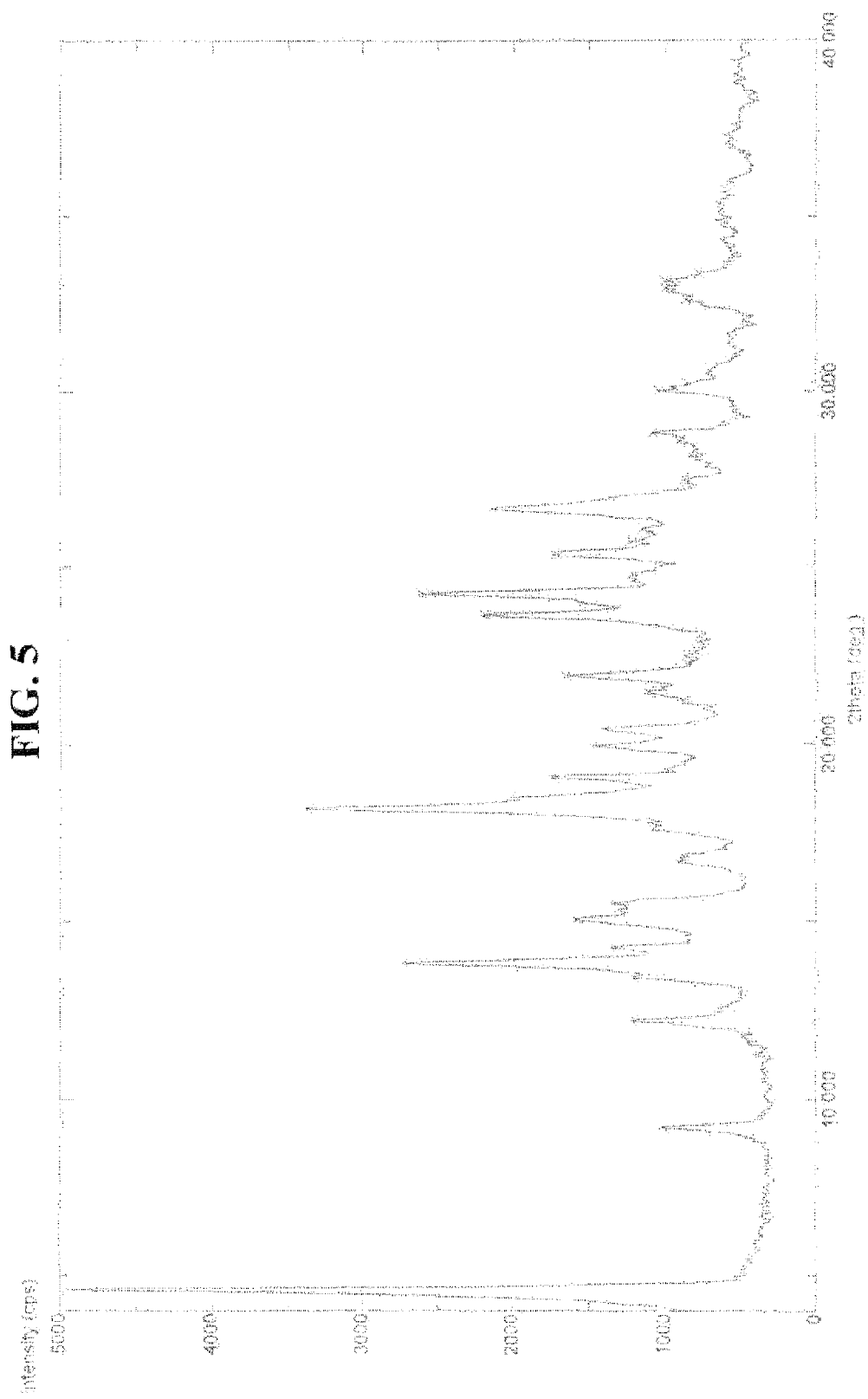
FIG. 5 is a powder X-ray diffraction (XRPD) pattern of the anhydrous crystalline form of phosphate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine according to the present invention.

In a further embodiment of the invention disclosed anhydrous crystalline form of phosphate salt of (2R) 4-oxo-4-[3-(trifluoromethyl)-5,6-dihydro[1,2,4]triazol o[4,3-a]pyrazin-7(8H)-yl]-1-(2,4,5-trifluorophenyl)butan-2-amine. It is also characterized by an XPRD peaks at about 4.6, 13.84, 15.05, 18.21, 24.25°±0.2 degrees 2θ. The anhydrous crystalline form further characterized by an additional XPRD peaks at about 13.45, 14.28, 15.52, 18.52, 19.09, 21.92, 23.63, 25.36, 26.67°±0.2° degrees 2θ. (FIG. 5)

Step-(h)

The compound of formula (Ib) having chiral purity≧70% as obtained in step (g) above, its chiral enrichment was done by using suitable solvents.

The suitable solvents used in step-(h) may be selected from alcohols like methanol, ethanol, isopropanol, butanol, 1,2-dimethoxy ethanol, 2-methoxy ethanol, 2-ethoxy ethanol, ethylene glycol and the like, esters like ethyl acetate, isopropyl acetate & the like, chlorinated solvents like chloroform, dichloromethane & the like, nitrites like acetonitrile & the like, hydrocarbons like toluene, xylene, chlorobenzene & the like, ketones like acetone & the like, ethers like diethyl ether, 1,4-dioxane, DIPE, MTBE, THF & the like, aprotic polar solvents such as DMF, DMSO, DMA & the like, water and suitable mixtures of one or more of the solvents described above.

The suitable mixtures of the solvent used for chiral enrichment may be selected from water: IPA; DMSO: Ethanol; DMSO: IPA; DMSO: ethyl acetate; water:acetonitrile: IPA.

The suitable mixtures of solvents used for chiral enrichment, & the preferred ratio of mixtures of the solvent used may be selected from water:IPA (1:20); DMSO:ethanol (1:4); DMSO:IPA (1:1); DMSO:ethyl acetate (1:0.5); water:acetonitrile:IPA (1:1.4:2.8).

The compound of formula (Ia) prepared according to the present invention, preferably have a purity of at least 96%, more preferably at least 98%.

It has surprisingly been found according to the invention that phosphate salt of (2R) 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine obtained by process disclosed herein was in its hydrated crystalline form having a characteristic XRD pattern different from those disclosed earlier.

Figure 6:
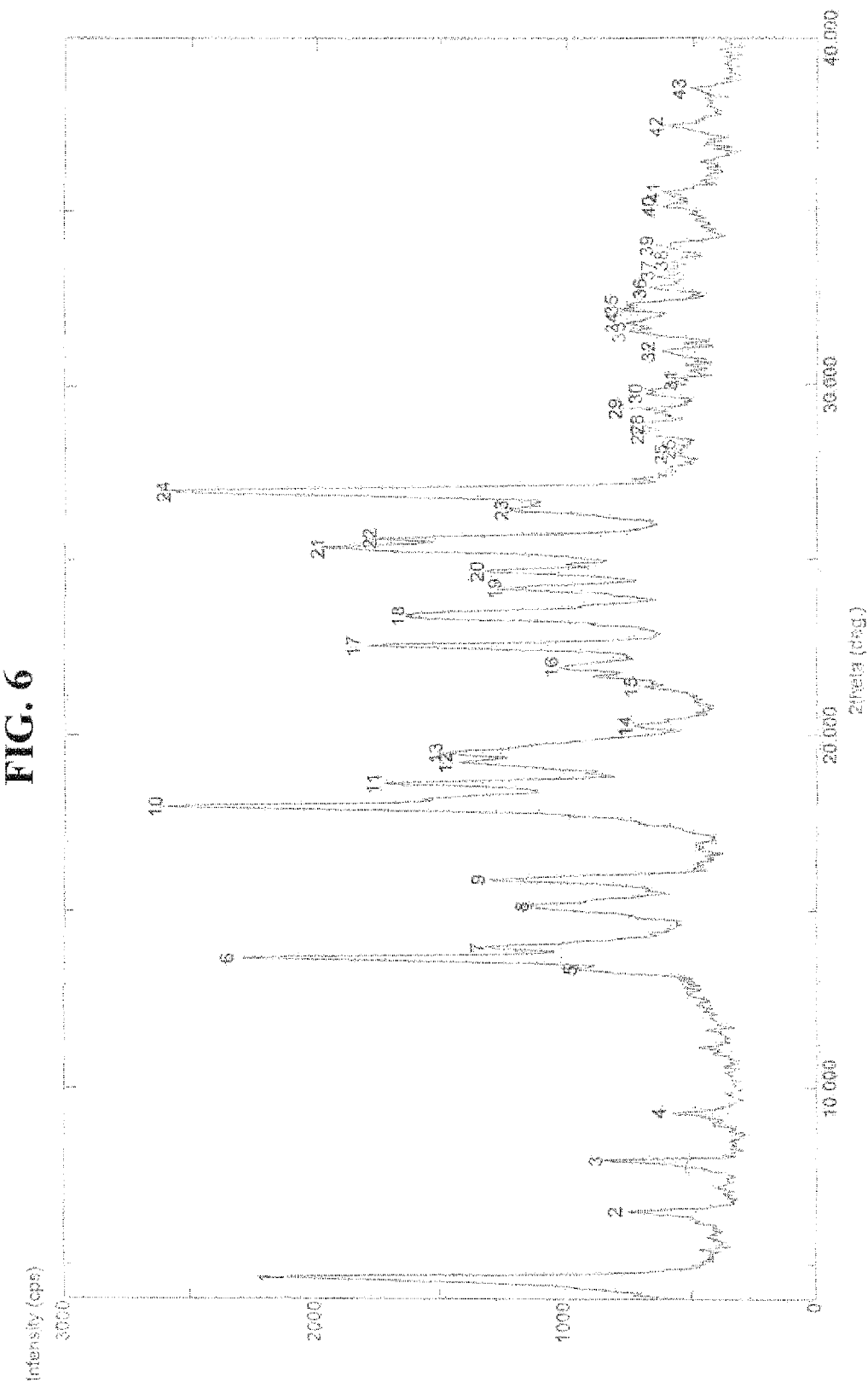
FIG. 6 is a powder X-ray diffraction (XRPD) pattern of the novel hydrated crystalline form of phosphate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine according to the present invention.

It is also characterized by an XPRD peaks at about 4.61, 6.50, 7.93, 9.30, 13.68, 15.88, 22.54, 25.33, 26.97°±0.2 degrees 2θ. The crystalline form further characterized by an additional XPRD peaks at about 13.99, 15.12, 18.63, 19.22, 21.93, 23.38, 25.61°±0.2° degrees 2θ. (FIG. 6)

In a preferred embodiment of the invention the (2R) 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine obtained in a crystalline hydrated form.

The phosphate salt of (2R) 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine initially shows improved stability, flowability and at least as much biological properties in appropriate diabetic animal model.

Furthermore, enantiomerically enriched unwanted isomer of β-amino acid derivatives of formula (VII) which is obtained in resolution step-(d) can be racemized either by treating with a base which may be selected from suitable inorganic or organic base, preferably the base used is selected from NaOH, KOH, NaH, potassium t-butoxide, or by following the racemization strategies as shown in scheme 2. Racemic β-amino acid derivatives of formula (VI) in scheme-2 can be further resolved by using suitable resolving agents as mentioned above to get β-amino acid derivatives of formula (I) in high chemical and chiral purity.

Naturally, such resolution occurs with the formation of solid diastereomeric salt, such salts are crystalline in nature and have potential to exhibit polymorphism.

Racemization Strategies:

1. Racemization of enantiomerically enriched unwanted isomer of β-amino acid derivatives of formula (VII) can be affected by activating amine with strong electron withdrawing groups (e.g. trifluoroacetyl, mesyl, tosyl, trifluoromethane sulfonyl etc.)

2. Racemization via Schiff base formation.

β-amino acid derivatives of formula (VII) was reacted with suitable acid chlorides such as acetyl chloride, trifluoroacetyl chloride, methanesulfonyl chloride, trifluoromethane sulfonyl and like or suitable acid anhydrides such as, trifluoroacetic anhydride and like, by standard techniques reported in the literature provides the compound of formula (VIII) (See for e.g. Protection and Deprotection of amines in Text book-Title: Protective Groups in Organic Synthesis, 3$^{rd}$ Edition, John Wiley & Sons, By-T. W. Grene and Peter G. M. Wuts). Deprotection was done by standard techniques reported such as in the above mentioned reference.

Similarly, β-amino acid derivatives and of formula (VII) was reacted with suitable aldehydes such as, benzaldehyde, p-nitrobenzaldehyde and the like, by standard techniques reported in the literature to provide the compound of formula (IX) (See for e.g. Protection and Deprotection of amines in Text book-Title: Protective Groups in Organic Synthesis, 3$^{rd}$ Edition, John Wiley & Sons, By-T. W. Grene and Peter G. M. Wuts). Deprotection was done by standard techniques such as those reported in the above mentioned reference.

Scheme 2: Racemization strategies

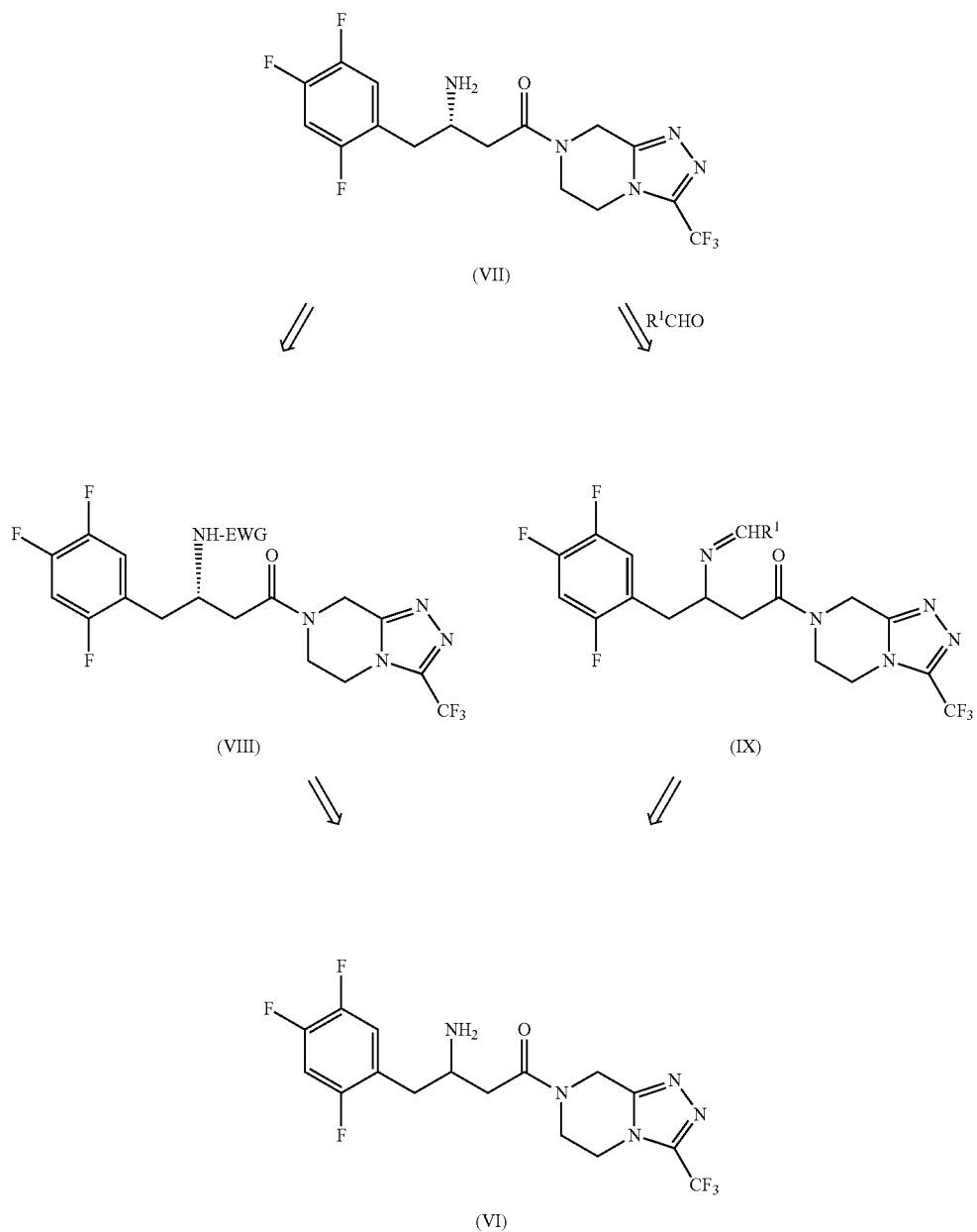

In one of the embodiment of the invention is disclosed a novel compound 3-hydroxy-1-(3-(trifluoromethyl)-5,6-dihydro-[1,2,4]triazolo[4,3-a]pyrazin-7(8H)-yl)-4-(2,4,5-trifluorophenyl)butan-1-one of formula (X), an impurity generated during the process as described above.

In another aspect, the invention encompasses a process for synthesizing the compound of formula (X) as described in scheme 3, whereby a metal ion salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one of formula (IV) or its derivative, is reduced by using suitable borane containing reducing agent as described earlier in absence or presence of a suitable acid in a suitable solvent to get 3-hydroxy-1-(3-(trifluoromethyl)-5,6-dihydro-[1,2,4]triazolo[4,3-a]pyrazin-7(8H)-yl)-4-(2,4,5-trifluorophenyl)butan-1-one of formula (X).

Scheme-3:

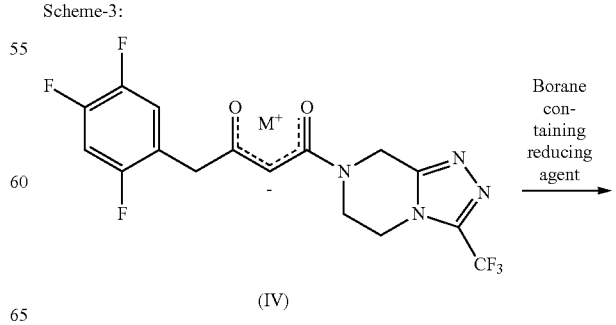

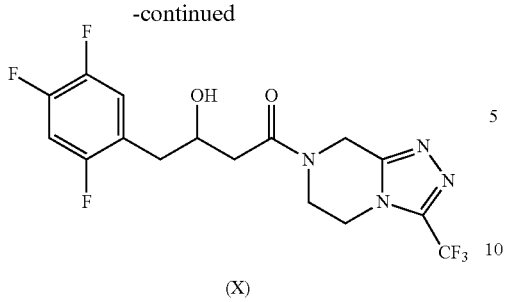

(X)

Optionally, 4-oxo-4-[3-(trifluoromethyl)-5,6-dihydro[1,2,4]triazolo[4,3-a]pyrazin-7(8H)-yl]-1-(2,4,5-trifluorophenyl)butan-2-one or its derivative is reduced by using a suitable borane containing reducing agent as earlier, in absence or presence of an acid in a suitable solvent to get 3-hydroxy-1-(3-(trifluoromethyl)-5,6-dihydro-[1,2,4]triazolo[4,3-a]pyrazin-7(8H)-yl)-4-(2,4,5-trifluorophenyl) butan-1-one.

Borane containing reducing agents include borohydride reducing agents such as, $NaBH_4$, $NaCNBH_4$, $Na(OAc)_3BH$, $LiBH_4$, $KBH_4$, $Na(OMe)_3BH$, $K(OiPr)_3BH$, 9-borabicyclo[3.3.1]nonane (9-BBN), (R) or (S)—B-isopinocamphenyl-9-borabicyclo[3,3,1]nonane; $BH_3$ complexes such as, $BH_3$-ammonia, $BH_3$-t-Bu amine, $BH_3$-triethylamine, $BH_3$-trimethylamine, $BH_3$-pyridine, $BH_3$-pyrrole, $BH_3$-piperazine, $BH_3$-piperidine; borane ether complex such as $BH_3$-THF; borane phosphine complexes such as $BH_3$-triphenylphosphine complex; borane sulfide complexes such as borane methylsulfide complex, borane 1,4-oxathiane.

Above disclosed Borane containing reducing agents is first reacted with a suitable acid selected from inorganic acids such as HCl, $H_2SO_4$; or organic acids selected from lower alkyl acid such as $CH_3COOH$, $CH_3CH_2COOH$; lower haloalkyl acid such as $CF_3COOH$, dichloroacetic acid; phenyl or substituted phenyl acid such as benzoic acid; loweralkyl sulfonic acid such as $CH_3SO_3H$, $C_2H_5SO_3H$; haloalkyl sulfonic acid such as $CF_3SO_3H$; phenyl sulfonic acid such as $C_6H_5SO_3H$; loweralkyl substituted phenyl sulfonic acid or naphthyl sulfonic acid; phosophoric acid, lower alkyl phosphonic acid such as methylphosphonic acid, phenylphosphonic acid, $BF_3.OEt_2$, tartaric acid, modified tartaric acid, camphorsulfonic acid and the like.

The suitable solvent(s) used for the formation of compound of formula (X) may be selected from alcohols like methanol, ethanol, isopropanol, butanol, 1,2-dimethoxy ethanol, 2-methoxy ethanol, 2-ethoxy ethanol and ethylene glycol; ethers like diethyl ether, 1,4-dioxane, dimethoxy ethane, DIPE, MTBE, THF, aprotic polar solvents such as DMF, DMSO, DMA and their suitable mixtures.

The compound of formula (X) may be used as an internal or external reference standard. The compound in a relatively pure state can be used as a reference standard" (a "reference marker is similar to a reference standard but it is used for qualitative analysis) to quantify the amount of the compound in an unknown mixture. When the compound is used as an "external standard" a solution of a known concentration of the compound is analyzed by the same technique as the unknown mixture.

In one embodiment of the invention is disclosed a pharmaceutical composition of compound of formula (I) or its pharmaceutically acceptable salts together with a liquid or solid carrier, excipients as is known in the art wherein the compound for formula (I) or its pharmaceutically acceptable salts is produced by any one of the above disclosed processes. The compound of formula (I) is generically known as Sitagliptin.

The invention is further exemplified by the following non-limiting examples, which are illustrative representing the preferred modes of carrying out the invention. The invention's scope is not limited to these specific embodiments only but should be read in conjunction with what is disclosed anywhere else in the specification together with those information and knowledge which are within the general understanding of a person skilled in the art.

Example 1

Preparation of Sodium salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one To a dry, 500 mL round bottom flask was charged 2,4,5-trifluorophenylacetic acid (25 g), Meldrum's acid (20.85 g), dimethylaminopyridine (1.28 g) and acetonitrile (80 mL) at 25-30° C. To the clear solution N,N-diisopropylethyl amine (DIPEA, 49.4 mL) was added slowly at 30-50° C. After that pivaloyl chloride (17.3 g) is added drop wise at 30-55° C. It was stirred for 4.5 h at 45-50° C. 3-(trifluoromethyl)-5,6,7,8-tetrahydro[1,2,4]triazolo[4,3-a]pyrazin.HCl (30 g) was added into the reaction mixture at 40 to 50° C. followed by dropwise addition of trifluoroacetic acid (3.0 mL). It was stirred for 6 h at 50 to 55° C. The solution was cooled to 0 to 5° C. and basified by adding dilute aq. NaOH solution till alkaline pH. It was stirred for 15-60 min. at 0 to 5° C. Solid salt of the title compound was filtered and washed with cold water. It was dried at reduced pressure. (Wt.-33.9 g, % Y-63.4%, % Purity by HPLC-98.4%).

Example 2

Preparation of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one via meldrum acid adduct Step-1:
A dry, 100 mL round bottom flask was charged with 2,4,5-trifluorophenylacetic acid (5 g), DCM (15 mL) and DMF 1-2 drops. To the reaction mixture oxalyl chloride (3.84 g) dissolved in DCM (10 mL) was added slowly at 20-25° C. It was stirred for 2 h at 20-25° C. After that the solvent was distilled out and also excess of oxalyl chloride to obtain green coloured crude acid chloride compound. It was dissolved in DCM and added slowly to a mixture of Meldrum's acid (4.0 g) and collidine (6.36 g) in DCM (27 mL) at −5 to 0° C. under $N_2$ gas atmosphere. Reaction mixture was stirred at 0° C. for 1 h. Then 35% conc. HCl solution was added at 0-5° C. It was transferred into a separating funnel. The layers were separated and organic layer was extracted twice with dilute aq. NaOH solution. The combined basic aqueous layers were acidified with 35% conc. HCl. Solid 5-[1-hydroxy-2-(2,4,5-trifluorophenyl)ethylidene]-2,2-dimethyl-1,3-dioxane-4,6-dione was precipitated. It was filtered, washed with water and dried under reduced pressure. Wt. of the product 6.0 g, % Yield-72%.

Step-2:
In a 50 mL three neck round bottom flask isopropyl acetate (20 ml), 3-(trifluoromethyl)-5,6,7,8-tetrahydro[1,2,4]triazolo[4,3-a]pyrazin.HCl (1.45 g), N,N-diisopropylethyl amine (DIPEA, 0.85 g) and 5-[1-hydroxy-2-(2,4,5-trifluorophenyl)ethylidene]-2,2-dimethyl-1,3-dioxane-4,6-dione (2.0 g) were charged at 25-30° C. It was heated to 85° C. and stirred for 3-5 h at 85-87° C. The solution was cooled to 25 to 30° C. To the reaction mixture water was added. It was transferred into a separating funnel. The layers were separated. The organic layer was washed with water. It was dried over anhydrous sodium sulfate & concentrated till 5 mL solution remains in the flask. Then n-heptane (3 mL) was added. It was stirred for 24 h at 25-30° C. Oily mass separated, on decanting the solvent. (Wt.-1.2 g, % Y-50%, % Purity by HPLC-81.5%).

Example 3

Preparation of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one via meldrum acid adduct Step-1:
To a dry, 100 mL round bottom flask were charged 2,4,5-trifluorophenylacetic acid (10 g), DCM (40 mL) and DMF (0.4 mL). To the reaction mixture oxalyl chloride (13.2 g) dissolved in DCM (10 mL) was added slowly at 20-25° C. It was stirred for 4 h at 20-25° C. After that solvent and excess oxalyl chloride was distilled out to obtain green coloured crude acid chloride compound. It was dissolved in DCM and added slowly to a mixture of Meldrum's acid (7.9 g) and collidine (13.3 g) in DCM (70 mL) at −5 to 0° C. under $N_2$ gas atmosphere. Reaction mixture was stirred at 25-30° C. for 4 h. Then 35% conc. HCl solution was added at 0-5° C. It was transferred into a separating funnel. The layers were separated and organic layer was extracted twice with dilute aq. NaOH solution. The combined basic aqueous layers were acidified with 35% conc. HCl solution. Product was extracted twice with ethyl acetate. The organic layer was dried over anhydrous sodium sulfate. Distilled out the solvent under reduced pressure to obtain solid 5-[1-hydroxy-2-(2,4,5-trifluorophenyl)ethylidine]-2,2-dimethyl-1,3-dioxane-4,6-dione Wt. of the product 6.8 g; % Yield-41%; and % purity by HPLC-95.8%.

Step-2:
In a 50 mL three neck round bottom flask toluene (20 ml), 3-(trifluoromethyl)-5,6,7,8-tetrahydro[1,2,4]triazolo[4,3-a]pyrazin.HCl (1.45 g), N,N-diisopropylethyl amine (DIPEA, 0.85 g) and 5-[1-hydroxy-2-(2,4,5-trifluorophenyl)ethylidine]-2,2-dimethyl-1,3-dioxane-4,6-dione (1.6 g) were charged at 25-30° C. It was heated to reflux temperature and stirred for 8 h at reflux temperature. Distilled out toluene at reduced pressure on Buchi rotavapour. To the residue isopropyl acetate and water were added. It was transferred into a separating funnel. The layers were separated. The organic layer was washed with satd. sodium bicarbonate solution and water. It was dried over anhydrous sodium sulfate. Distilled out the solvent at reduced pressure on Buchi Rotavapour. Then n-heptane was added. It was stirred for 16 h at 25-30° C. Solid was separated. It was filtered and washed with n-heptane. Dry wt.-1.2 g, % Y-60%, % Purity by HPLC-84.7%.

Example 4

Preparation of Sodium salt of 4-oxo-4-[3-(trifluoromethyl)-5,6-dihydro[1,2,4]triazolo[4,3-a]pyrazin-7(8H)-yl]-4-(2,4,5-trifluorophenyl)butan-2-one To a dry, 500 mL round bottom flask was charged with 2,4,5-trifluorophenylacetic acid (25 g), Meldrum's acid (20.85 g), dimethylaminopyridine (1.28 g) and acetonitrile (80 mL) at 25-30° C. To the clear solution N,N-diisopropylethyl amine (DIPEA, 49.4 mL) was added slowly at 30-50° C. After that pivaloyl chloride (17.3 g) was added drop wise at 45-50° C. It was stirred for 4.5 h at 45-50° C. 3-(trifluoromethyl)-5,6,7,8-tetrahydro[1,2,4]triazolo[4,3-a]pyrazin.HCl (30 g) was added into the reaction mixture at 40 to 50° C. followed by dropwise addition of trifluoroacetic acid (3.0 mL). It was stirred for 6 h at 50 to 55° C. The solution was cooled to 0 to 5° C. and basified by adding dilute aq. NaOH solution up to more than 10 pH. It was stirred for 15-60 min. at 0 to 5° C. Solid salt of the title compound was filtered and washed with cold water. It was dried at reduced pressure. (Wt.-34.1 g, % Y-63.8%, % Purity by HPLC-97.7%). % of Na by ion chromatography-4.88%.

$^1$H NMR (400 MHz, $CD_3CN$): δ 3.78 (s, 2H, minor), 3.80 (s, 2H, major), 3.83 (m, 2H, major), 3.90 (s, 2H, minor), 3.91 (s, 2H, major), 3.99 (m, 2H, minor), 4.12 (m, 211, minor), 4.15 (m, 2H, major), 4.80 (s, 2H, minor), 4.90 (S, 2H, minor), 6.97-7.01 (m, 1H), 7.09-7.13 (m, 1H), 7.15-7.20 (m, 1H), 7.24-7.31 (m, 1H).
(Assignment are denoted for major/minor/both isomers)
ESI-MS: 428.8 (M+Na)$^+$ Example 5

Preparation of Sodium salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one To a dry, 10 L round bottom three neck flask was charged 2,4,5-trifluorophenylacetic acid (212.5 g), Meldrum's acid (177.2 g), dimethylaminopyridine (11 g) and acetonitrile (680 mL) at 25-30° C. To the clear solution N,N-diisopropylethyl amine (DIPEA, 492 mL) was added slowly at 30-50° C. After that pivaloyl chloride (17.3 g) was added drop wise at 45-50° C. over a period of 2.5 h. It was stirred for 3-4 h at 45-50° C. 3-(trifluoromethyl)-5,6,7,8-tetrahydro[1,2,4]triazolo[4,3-a]pyrazin.HCl (255 g) was added into the reaction mixture at 40 to 50° C. followed by dropwise addition of trifluoroacetic acid (25.5 mL). It was stirred for 6 h at 50 to 55° C. The solution was cooled to 0 to 5° C. and basified by adding slowly dilute aq. NaOH solution (266 g dissolved in 3.4 L water) till alkaline pH. It was stirred for 15-60 min. at 0 to 5° C. Solid salt of the title compound was filtered and washed with cold water & dried at reduced pressure. (Wt.-349.7 g, % Y-72.8%, % Purity by HPLC-96.7%, % Water by KF-4.19%). % Na by Ion chromatography-5.03%.

Example 6

Preparation of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one from it's Sodium salt Sodium salt of 4-oxo-4-[3-(trifluoromethyl)-5,6-dihydro [1,2,4]triazolo[4,3-a]pyrazin-7(8H)-yl]-1-(2,4,5-trifluorophenyl)butan-2-one was stirred in a mixture of ethyl acetate and 10% aq. HCl solution at 25-30° C. for 15-30 min. & transferred into a separating funnel. The organic layer was separated. It was washed with water and brine solution. It was dried over anhydrous sodium sulfate. Solvent was distilled out at reduced pressure on Buchi rotavapour. Thick liquid product was obtained (Wt.-8.5 g, % Y-90%, % Purity by HPLC-95.8%).

Example 7

Preparation of Calcium salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one In a 25 mL round bottom three neck flask 4-oxo-4-[3-(trifluoromethyl)-5,6-dihydro[1,2,4]triazolo[4,3-a]pyrazin- 7(8H)-yl]-1-(2,4,5-trifluorophenyl)butan-2-one (0.8 g) was dissolved in MeOH. To the reaction mixture dil. aq. NaOH solution (78 mg) was added. It was stirred for 10-15 min. at 25-30° C. Then aq. solution of calcium acetate (155 mg) at 25-30° C. was added to it. It was heated to 50-60° C. and stirred for 30-60 min. It was cooled to 25-30° C. Solid salt was filtered and washed with aq. MeOH. Wt. of Calcium salt-0.5 g, % Purity by HPLC-99.3%. % Ca by Ion chromatography-4.7%.

Example 8

Preparation of Magnesium salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one from it's Sodium salt In a 25 mL round bottom three neck flask, sodium salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one (1.0 g) was dissolved in MeOH at reflux temperature. To the reaction mixture aq. solution of magnesium chloride (115 mg) was added. It was stirred for 10-15 min. at reflux temperature. It was cooled to 25-30° C. Solid salt was filtered and washed with aq. MeOH. Wt. of magnesium salt-0.72 g; % Purity by HPLC-98.4%; % $H_2O$ by KF-4.3%.

Example 9

Preparation of Magnesium salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one from it's Sodium salt In a 25 mL round bottom three neck flask, sodium salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one (1.0 g) was dissolved in MeOH at reflux temperature. To the reaction mixture aq. solution of magnesium acetate (260 mg) was added. It was stirred for 10-15 min. at reflux temperature. It was cooled to 25-30° C. Solid salt was filtered and washed with aq. MeOH. Wt. of magnesium salt-0.62 g; % Purity by HPLC-99.0%; % $H_2O$ by KF-3.5%.

Example 10

Preparation of Copper salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one In a 25 mL round bottom three neck flask sodium salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one (1.0 g) was dissolved in MeOH at reflux temperature. To the reaction mixture aq. solution of copper sulfate pentahydrate (307 mg) was added. It was stirred for 10-15 min. at reflux temperature. It was cooled to 25-30° C. Solid salt was filtered and washed with aq. MeOH. Wt. of copper salt-0.66 g; % Purity by HPLC-95.5%.

Example 11

Preparation of (2E/Z)-4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine In a 100 mL round bottom flask, sodium salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one (8.0 g) and methanol were charged. To the reaction mixture ammonium acetate (4.2 g) and aq. $NH_4OH$ solution (2.4 mL) mixed in methanol (8 mL) was added drop wise at 25-30° C. It was heated to reflux temperature and stirred for 6 h. Reaction mixture was cooled to 0-5° C. and stirred for 30-90 minutes. Solid product was filtered and washed with cold water. It was dried. (Wt.-5.9 g, % Y-76.7%, % Purity by HPLC-96.5%).

Example 12

Preparation of (2E/Z)-4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine In a 100 mL round bottom flask Sodium salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one (2.0 g), acetic acid (0.3 mL) and methanol (10 mL) were charged. It was heated to 60-65° C. To the reaction mixture ammonium formate (1.8 g) and aq. $NH_4OH$ solution (0.6 mL) was added at 60-65° C. It was heated to reflux temperature and stirred for 5 h. Reaction mixture was cooled to 25-30° C. and stirred for 30-90 minutes. Solid product was filtered and washed with cold water. The crude product was stirred with ethyl acetate at reflux temperature. It was cooled to 25-30° C. Solid product was filtered and washed with cold ethyl acetate. It was dried. (Wt.-1.5 g; % Y-79.3%; % Purity by HPLC-99.3%).

Example 13

Preparation of (2E/Z)-4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine In a 100 mL round bottom flask, Sodium salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one (2.0 g), acetic acid (0.3 mL) and methanol (15 mL) were charged. It was heated to 60-65° C. To the reaction ammonium carbonate (2.2 g) was added at 60-65° C. It was heated to reflux temperature and stirred for 5 h. Reaction mixture was cooled to 25-30° C. and stirred for 30-90 minutes. Solid product was filtered and washed with cold water. The crude product was stirred with ethyl acetate at reflux temperature. It was cooled to 25-30° C. Solid, product was filtered and washed with cold ethyl acetate. It was dried. (Wt.-1.0 g; % Y-53%; % Purity by HPLC-99.7%).

Example 14

Preparation of (2E/Z)-4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine In a 1 L round bottom flask, Sodium salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one (100 g), methanol (200 mL) and acetic acid (12 mL) were charged. To the reaction mixture ammonium acetate (89.7 g) and aq. $NH_4OH$ solution (30 mL) was added at 25-30° C. It was heated to reflux temperature and stirred for 8 h. Reaction mixture was cooled to 25-30° C. and stirred for 30-60 minutes. Solid product was filtered and washed with cold water and ethyl acetate. Wet cake was stirred with ethyl acetate at reflux temperature. It was cooled to 25-30° C. Solid product

Example 15

Preparation of (2E/Z)-4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine In a 250 mL round bottom flask Sodium salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one (20 g), methanol (60 mL) and acetic acid (3 mL) were charged. To the reaction mixture ammonium acetate (10.7 g) and aq. $NH_4OH$ solution (6 mL) was added at 60-65° C. It was stirred for 6 h at reflux temperature. Reaction mixture was cooled to 0-5° C. and stirred for 30-60 minutes. Solid product was filtered and washed with cold water. It was dried. (Wt.-16.7 g, % Y-88.4%, % Purity by HPLC-90.2%)

Example 16

Preparation of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 250 mL round bottom flask THF (110 mL) was taken. It was cooled to less than −5° C. and $NaBH_4$ (2.81 g) was added. After that methanesulfonic acid (17.8 g) was added dropwise at less than −5° C. over a period of 1 h. 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine (10.0 g) is mixed in a solvent mixture of THF (25 mL) and IPA (11 mL) and added into the reaction mixture, keeping the temperature below 0° C. It was stirred for 4-6 h below 5° C. After usual work-up procedure, product was extracted in a suitable solvent. Extract was washed and dried over anhydrous sodium sulfate. Solvent was evaporated at reduced pressure to obtain the product. (Wt.-9.5 g, % Y-94.5%, % Purity by HPLC-94.6%).

Example 17

Preparation of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 250 mL round bottom flask THF (75 mL) was taken. It was cooled to −15 to −10° C. and $NaBH_4$ (1.87 g) was added. After that methanesulfonic acid (11.8 g) was added dropwise at −15 to −10° C. over a period of 30-45 min. 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine (10.0 g) is mixed in a solvent mixture of THF and IPA and added into the reaction mixture, keeping the temperature −10 to −5° C. It was stirred for 30-60 min. at −10 to −5° C. Reaction mixture was poured into cold water. It was basified by adding aq. ammonia solution. Product was extracted in ethyl acetate. The organic layer was collected. It was washed with water and dried over anhydrous sodium sulfate. Solvent was evaporated at reduced pressure to obtain the product. (Wt.-9.15 g; % Y-91%; % Purity by HPLC-88.6%).

Example 18

Preparation of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 2 L round bottom flask dry THF (450 mL) was taken. It was cooled to −15 to −10° C. and $NaBH_4$ (11.2 g) was added. After that methanesulfonic acid (71.1 g) was added dropwise at −15 to −5° C. over a period of 2.5 h. Separately, 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine (40.0 g) was mixed in a solvent mixture of dry THF (100 mL) and IPA (44 mL) and added into the reaction mixture over a period of 45-60 min. at −10 to −5° C. It was stirred for 30-60 min. at −10 to −5° C. Reaction mixture was poured into cold water. It was basified by adding 25% aq. ammonia solution. Product was extracted in an ethyl acetate. The organic layer was collected and combined. It was washed with water and brine solution. It was dried over anhydrous sodium sulfate. Solvent was evaporated at reduced pressure to obtain the product. (Wt.-41.5 g; % Y-100%; % Purity by HPLC-94.5%; % $H_2O$ by KF-4.58%).

Example 19

Preparation of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 50 mL round bottom flask dry THF (17 mL) was taken. It was cooled to −10° C. and 2.0 M Borane methyl sulfide complex solutions in THF (7.41 mL) were added. After that methanesulfonic acid (2.4 mL) was added dropwise at −10° C. over a period of 15-30 min. 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine (2.0 g) is mixed in a solvent mixture of THF (5.0 mL) and IPA (5.0 mL) and added into the reaction mixture, keeping the temperature between −10 to −5. It was stirred for 4 h at −10 to −5° C. Reaction mixture was poured into cold water. It was basified by adding aq. ammonia solution. Product was extracted in ethyl acetate. The organic layer was collected, was washed with water and dried over anhydrous sodium sulfate. Solvent was evaporated at reduced pressure to obtain the product. (Wt.-2.0 g, % Y-100%, % $H_2O$-5.18%, % Purity by HPLC-96.6%). XRD-amorphous-FIG. 1

Example 20

Preparation of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 250 mL round bottom flask 1.0 M Borane tetrahydrofuran (37 mL) was taken. It was cooled to −10° C. and TEA (5.15 mL) was added dropwise at −10 to 5° C. After 30 min. methanesulfonic acid (6.0 mL) was added dropwise at −10 to 5° C. over a period of 15-30 min. 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine (5.0 g) was added in small portions into the reaction mixture, keeping the temperature between −10 to −5° C. It was stirred for 1 h at −10 to −5° C. Reaction mixture was poured into cold water. It was basified by adding aq. ammonia solution. Product was extracted in ethyl acetate. The organic layer was collected. It was washed with water and dried over anhydrous sodium sulfate. Solvent was evaporated at reduced pressure to obtain the product. (Wt.-4.2 g; % Y-83.6%; % Purity by HPLC-31%).

Example 21

Preparation of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 250 mL round bottom flask 1.0 M Borane tetrahydrofuran (37 mL) was taken. It was cooled to −10° C. and piperidine (3.14 g) was added dropwise at −10 to 5° C. After 30 min. methanesulfonic acid (6.0 mL) was added dropwise at −10 to 5° C. over a period of 15-30 min. Separately, 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine (5.0 g) was added in small portions into the reaction mixture, keeping the temperature between −10 to −5° C. It was stirred for 1 h at −10 to −5° C. Reaction mixture was poured into cold water. It was basified by adding aq. ammonia solution. Product was extracted in an ethyl acetate. The organic layer was collected. It was washed with water and dried over anhydrous sodium sulfate. Solvent was evaporated at reduced pressure to obtain the product. (Wt.-4.1 g, % Y-81.0%, % Purity by HPLC-84.5%).

Example 22

Preparation of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 250 mL round bottom flask dry THF (94 mL) was taken. It was cooled to −10° C. and NaBH$_4$ (2.38 g) was added. After that sulfuric acid (6.0 g) was added dropwise at −5 to 0° C. over a period of 15-30 min. Separately, 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine (5.0 g) was mixed in a solvent mixture of THF (12.5 mL) and water (1.7 mL) and added into the reaction mixture, keeping the temperature between −2 to 0. It was stirred for 1 h at −2 to 0° C. Reaction mixture was poured into cold water. It was basified by adding aq. ammonia solution. Product was extracted in ethyl acetate. The organic layer was collected. It was washed with water and dried over anhydrous sodium sulfate. Solvent was evaporated at reduced pressure to obtain the product. (Wt.-4.8 g, % Y-95.6%, % Purity by HPLC-90.8%).

Example 23

Preparation of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 250 mL round bottom flask dry THF (56 mL) was taken. It was cooled to −10° C. and NaBH$_4$ (1.4 g) was added. After that benzenesulfonic acid (14.6 g) dissolved in THF (20 mL) was added dropwise at −10 to 5° C. over a period of 30-60 min. 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine (5.0 g) was mixed in a solvent mixture of THF (12.5 mL) and IPA (5.5 mL) and added into the reaction mixture, keeping the temperature between −10 to 5. It was stirred for 5 h at −10 to 0° C. Reaction mixture was poured into cold water. It was basified by adding aq. ammonia solution. Product was extracted in ethyl acetate. The organic layer was collected. It was washed with water and dried over anhydrous sodium sulfate. Solvent was evaporated at reduced pressure to obtain the product. (Wt.-5.5 g; % Y-95.6%; % Purity by HPLC-62.5%).

Example 24

Preparation of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 250 mL round bottom flask dry THF (35 mL) was taken. It was cooled to −10 to −5° C. and NaBH$_4$ (2.0 g) was added. After that acetic acid (33.7 mL) was added dropwise at −5 to 0° C. over a period of 15-30 min. 4-oxo-4-[3-(trifluoromethyl)-5,6-dihydro[1,2,4]triazol o[4,3-a]pyrazin-7(8H)-yl]-1-(2,4,5-trifluorophenyl)but-2-en-2-amine (5.0 g) was added into the reaction mixture, keeping the temperature between −2 to 0° C. It was stirred for 2-3 h at −5 to 0° C. Reaction mixture was poured into cold water. It was basified by adding aq. ammonia solution. Product was extracted in ethyl acetate. The organic layer was collected. It was washed with water and dried over anhydrous sodium sulfate. Solvent was evaporated at reduced pressure to obtain the product. (Wt.-4.2 g, % Y-83.6%, % Purity by HPLC-60.1%).

Example 25

Preparation of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 250 mL round bottom flask THF (75 mL) was taken. It was cooled to −8 to −5° C. and NaBH$_4$ (1.87 g) was added. After that trifluoroacetic acid (11.3 g) was added dropwise at −15 to −5° C. over a period of 30-45 min. Separately, 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine (5.0 g) was added in small portions into the reaction mixture, keeping the temperature between −10 to −5° C. It was stirred for 1 h at −10 to −0° C. Reaction mixture was poured into cold water. It was basified by adding aq. ammonia solution. Product was extracted in ethyl acetate. The organic layer was collected. It was washed with water and dried over anhydrous sodium sulfate. Solvent was evaporated at reduced pressure to obtain the product. (Wt.-4.9 g; % Y-97.6%; % Purity by HPLC-81.6%).

Example 26

Preparation of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 500 mL round bottom flask dry THF (112 mL) and NaBH$_4$ (2.81 g) were taken. It was cooled to −15 to −10° C. After that methanesulfonic acid (17.7 g) was added dropwise at −15 to −5° C. over a period of 1.5 h. 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine (10.0 g) was mixed in a solvent mixture of dry THF (25 mL) and IPA (11 mL) and added into the reaction mixture over a period of 45-60 min. at −10 to −5. It was stirred for 30-60 min. at −10 to −5° C. Reaction mixture was poured into cold 10% aq. HCl solution. It was basified by adding aq. NaHCO$_3$ solution. Product was extracted in ethyl acetate. The organic layer was collected, washed with water and brine solution. It was dried over anhydrous sodium sulfate. Solvent was evaporated at reduced pressure to obtain the product. (Wt.-12.4 g, % Purity by HPLC-94.9%).

Example 27

Preparation of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 100 mL round bottom flask dry THF (50 mL) was taken. It was cooled to −15 to −10° C. and NaBH$_4$ (1.1 g) was added. After that boron trifluoride etherate (10.9 g) was added dropwise at −15 to −5° C. over a period of 30 min. 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine (5.0 g) was mixed in a solvent mixture of dry THF (12.5 mL) and IPA (5.5 mL) and added into the reaction mixture over a period of 45-60 min. at −10 to −5° C. It was stirred for 2.5 h at −10 to −5° C. Reaction mixture was poured into cold water. It was basified by adding 25% aq. ammonia solution. Product was extracted in ethyl acetate. The organic layer was collected and combined. It was washed with water and brine solution. It was dried over anhydrous sodium sulfate. Solvent was evaporated at reduced pressure to obtain the product. (Wt.-4.81 g, % Y-95.8%, % Purity by HPLC-96.5%).

Example 28

Resolution of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine Dibenzoyl-D-tartaric acid salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was prepared by reacting Dibezoyl-D-tartaric acid monohydrate and 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in molar equivalent ratio in methanol. The salt was filtered off and filtrate was collected. Solvent was distilled out from the filtrate to obtain enantiomerically enriched desired isomer which was basified in aq. methanol by using NaHCO$_3$. Solvent was again distilled out. The residue was dissolved in ethyl acetate and washed with water and brine solution. Ethyl acetate extract was collected and dried over anhydrous sodium sulfate. Ethyl acetate was distilled out to obtain (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (% Purity by HPLC-88%, % Chiral purity by HPLC-90.0%).

Example 29

Resolution of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine Dibenzoyl-L-tartaric acid salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was prepared by reacting 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (1.0 mole) with Dibezoyl-L-tartaric acid monohydrate (1.18 molar equivalent) in IPA-methanol at 25-70° C. till solid mass precipitated out. The salt was filtered and washed with IPA; an enantiomerically enriched desired isomer was obtained. The salt was taken into ethyl acetate. It was basified with aq. NaHCO$_3$. Ethyl acetate layer was separated and washed with water and brine solution. Ethyl acetate extract was collected and dried over anhydrous sodium sulfate. Ethyl acetate was distilled out to obtain a mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (% Purity by HPLC-98%; % Chiral purity by HPLC of R-isomer 70%).

Example 30

Resolution of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 50 mL three neck flask MeOH (10 mL) and 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.0 g) were taken. It was stirred at room temperature to get clear solution. Dibenzoyl-L-tartaric acid monohydrate (1.84 g) was added into reaction mixture at room temperature. It was stirred for 2 h at room temperature. Solid salt was precipitated. The salt was filtered and washed with methanol; an enantiomerically enriched desired isomer was obtained (Wt.-0.905 g % Y-23.5%). The salt was taken into methanol. It was basified with aq. NaHCO$_3$. Distilled out solvent at reduced pressure. To the thick residue water (5 mL) was added. It was extracted twice with ethyl acetate and combined both the extracts. It was washed with water and brine solution. Ethyl acetate extract was collected and dried over anhydrous sodium sulfate. Ethyl acetate was distilled out to obtain a mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (% Y-23%, Purity by HPLC-98.7%, % Chiral purity by HPLC of R-isomer 77%).

Example 31

Resolution of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 50 mL three neck flask IPA (5 mL) and Dibenzoyl-L-tartaric acid monohydrate (1.84 g) were taken. It was heated to 60-65° C. 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.0 g, % purity-90.5%) dissolved in methanol (6 mL) was added into the reaction mixture at 60-65° C. It was stirred for 30 min. at 60-65° C. Solid salt was precipitated. It was gradually cooled to room temperature over a period of 2-3 h. The salt was filtered and washed with a mixture of IPA: MeOH (2:1, 10 mL). An enantiomerically enriched desired Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained (Wt.-1.72 g, % Y-45%, Purity by HPLC-99.3%, % Chiral purity by HPLC of R-isomer 81%).

In a similar manner an enantiomerically enriched desired Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was prepared by reacting dibenzoyl-L-tartaric acid monohydrate and 4-oxo-4-[3-(trifluoromethyl)-5,6-dihydro[1,2,4]triazolo[4,3-a]pyrazin-7(8H)-yl]-1-(2,4,5-trifluorophenyl)

butan-2-amine (% purity→90%) in a mole equivalent using different solvent mixtures under different conditions as given below:

1-(2,4,5-trifluorophenyl)butan-2-amine was obtained (Wt.-1.1 g, %Y-28.7%, Purity by HPLC-99.1%, % Chiral purity by HPLC of R-isomer 74%).

| Ex. No. | Solvent | Condition | % Purity & % Chiral purity | % Yield |
|---|---|---|---|---|
| 32. | Methanol-DIPE | Reflux to dissolve in MeOH, cool to 0-5° C., 8 h, no solid, DIPE added, 0-5° C., 4 h | 95.18% (76.4%) | 7.8% |
| 33. | Methanol-Toluene | 60-65° C., 1 h cool to 25-30° C., 42 h, solid | 97.8% (80.5%) | 8.16% |
| 34. | Methanol-Toluene | 60-65° C., 1 h, solid ppt then toluene was added cool to 25-30° C., 1 h, solid | 96.01% (76.6%) | 31.5% |
| 35. | Methanol-MIBK | 80-85° C., 3 h cool to 25-30° C., 24 h and 0-5° C., 6 h solid | 98.8% (73.7%) | 16.4% |
| 36. | t-BuOH—MeOH (10:1) | 60-65° C., 10 min. cool to 25-30° C., 1.5 h, solid | 98.03% (67.2%) | 57.5% |
| 37. | Dioxane-MeOH | 70° C., 2.0 h cool to 25-30° C., 3 h cool to 0-5° C., 1.0 h, solid | 99.1% (77.5%) | 34.8% |
| 38. | Methanol-MIBK | 70° C., 2.0 h cool to 25-30° C., 3 h, solid | 99.2% (76.8%) | 35.1% |
| 39. | Methanol-MIBK-Water | 70° C., 2.0 h cool to 25-30° C., 3 h, solid | 99.73% (78.9%) | 34.8% |

Example 40

Resolution of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 50 mL three neck flask IPA (5 mL) and Dibenzoyl-L-tartaric acid (1.75 g) were taken. It was heated to 60-65° C. 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.0 g, % purity-94%) dissolved in methanol (6 mL) was added into reaction mixture at 60-65. It was stirred for 60 min. at 60-65° C. Solid salt was precipitated. It was gradually cooled to room temperature over a period of 2 to 3 hrs. The salt was filtered and washed with a mixture of IPA: MeOH (2:1, 10 mL). An enantiomerically enriched desired Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained (Wt.-1.08 g, %Y-29%, Purity by HPLC-99.1%, % Chiral purity by HPLC of R-isomer 76.7%).

Example 41

Resolution of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 50 mL three neck flask IPA (5 mL), water (2 mL) and Dibenzoyl-L-tartaric acid monohydrate (1.84 g) were taken. It was heated to 40-45° C. 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.0 g, % purity-94%) dissolved in IPA (5 mL) was added into reaction mixture at 60-65° C. It was stirred for 1 h at 60-65° C. It was gradually cooled to room temperature. Then it was further cooled to 0-5° C. and stirred for 1 h. The salt was filtered and washed with cold IPA. An enantiomerically enriched desired Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained (Wt.-1.1 g, %Y-28.7%, Purity by HPLC-99.1%, % Chiral purity by HPLC of R-isomer 74%).

In a similar manner an enantiomerically enriched desired Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was prepared by reacting dibenzoyl-L-tartaric acid monohydrate and 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (% purity→90%) in a mole equivalent using different solvent mixtures under different conditions as given below:

| Ex. No. | Solvent | Condition | % Purity & % Chiral purity of R-isomer | % Yield |
|---|---|---|---|---|
| 42. | IPA-water (3 eq. to racemic sitagliptin) | 60-65° C., 1 h cool to 25-30° C., 1 h, solid | 99.5% (71.3%) | 41.4% |
| 43. | IPA-water (5 eq. to racemic sitagliptin) | 60-65° C., 1 h cool to 25-30° C., 1 h, solid | 99.0% (69.4%) | 42.2% |
| 44. | IPA-Dioxane | 60-65° C., 1 h cool to 0-5° C., 60 h, solid | 99.1% (75.4%) | 16.7% |
| 45. | IPA + 2-ME | 60-65° C., 1 h cool to 25-30° C., 24 h, solid | 99.4% (80.35%) | 23.2% |
| 46. | IPA + THF + water | 60-65° C., 1 h cool to 25-30° C., 1 h, solid | 96.1% (69.0%) | 24.1% |

Example 47

Resolution of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 50 mL three neck flask EtOH (5 mL) and Dibenzoyl-L-tartaric acid monohydrate (1.84 g) were taken. It was heated to 60-65° C. 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.0 g, % purity-93.8%) dissolved in EtOH (6 mL) was added into reaction mixture at 60-65° C. It was stirred for 1 h at 60-65° C. Solid salt was precipitated. It was gradually cooled to room temperature over a period of 2-3 h. The salt was filtered and washed with cold EtOH. An enantiomerically enriched desired Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained (Wt.-0.8 g, yield-20.9%, Purity by HPLC-99.6%, % Chiral purity by HPLC of R-isomer 78%).

In a similar manner an enantiomerically enriched desired Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was prepared by reacting dibenzoyl-L-tartaric acid monohydrate and 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (% purity→90%) in a mole equivalent using different solvents under different conditions as given below.

| Ex. No. | Solvent | Condition | % Purity & % Chiral purity | % Yield |
|---|---|---|---|---|
| 48. | EA | 60-65° C., 1 h cool to 0-5° C., 1 h, solid | 99.9% (77.2%) | 20.0% |
| 49 | Isoamyl alcohol | 60-65° C., 1 h cool to 0-5° C., 48 h, solid | 98.7% (70.0%) | 21.1% |
| 50 | EA-water | 60-65° C., 1 h cool to 0-5° C., 1.5 h, solid | 99.2% (77.6%) | 28.4% |
| 51 | Dioxane-water | 60-65° C., 1 h cool to 25-30° C., 24 h, solid | 98.7% (76.2%) | 34.5% |
| 52 | IPA + THF + water | 60-65° C., 1 h cool to 25-30° C., 1 h, solid | 96.1% (69.0%) | 24.1% |

Example 53

Resolution of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 100 mL three neck flask IPA (27 mL) and Dibenzoyl-L-tartaric acid monohydrate (1.84 g) were taken. It was heated to 60-65° C. 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.0 g, % purity-93.8%) dissolved in methanol (17 mL) was added into reaction mixture at 60-65° C. It was stirred for 60 min. at 60-65° C. Solid salt was precipitated. It was gradually cooled to room temperature over a period of 2-3 h. The salt was filtered and washed with a mixture of IPA: MeOH (2:1). An enantiomerically enriched desired Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained (Wt.-0.65 g, % Y-17%, Purity by HPLC-99.8%, % Chiral purity by HPLC of R-isomer 77. %).

Example 54

Resolution of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 50 mL three neck flask IPA (5 mL) and Dibenzoyl-L-tartaric acid monohydrate (1.1 g) were taken. It was heated to 60-65° C. 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.0 g, % purity-93.8%) dissolved in methanol (6 mL) was added into reaction mixture at 60-65° C. It was stirred for 60 min. at 60-65° C. Solid salt was precipitated. It was gradually cooled to room temperature over a period of 2-3 h. The salt was filtered and washed with a mixture of IPA: MeOH (2:1). An enantiomerically enriched desired Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained (Wt.-1.1 g, % Y-28.7%, Purity by HPLC-99.1%, % Chiral purity by HPLC of R-isomer 74%).

Example 55

Resolution of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 50 mL three neck flask IPA (5 mL) and Dibenzoyl-L-tartaric acid monohydrate (2.21 g) were taken. It was heated to 60-65° C. 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.0 g, % purity-93.8%) dissolved in methanol (6 mL) was added into reaction mixture at 60-65° C. It was stirred for 60 min. at 60-65° C. Solid salt was precipitated. It was gradually cooled to room temperature over a period of 2-3 h. The salt was filtered and washed with a mixture of IPA: MeOH (2:1). An enantiomerically enriched desired Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained (Wt.-2.38 g, % Y-62%, Purity by HPLC-98.6%, % chiral purity by HPLC of R-isomer 64.6%).

Example 56

Resolution of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 50 mL three neck flask IPA (5 mL) and Dibenzoyl-L-tartaric acid monohydrate (0.925 g) were taken. It was heated to 60-65° C. 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.0 g, % purity-93.8%) dissolved in methanol (6 mL) and formic acid (0.112 g) was added into reaction mixture at 60-65. It was stirred for 60 min. at 60-65° C. Solid salt was precipitated. It was gradually cooled to room temperature over a period of 2-3 h. The salt was filtered and washed with a mixture of IPA: MeOH (2:1). An enantiomerically enriched desired Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained (Wt.-1.32 g, % Y-34.6%, Purity by HPLC-99.6%, % Chiral purity by HPLC of R-isomer 75.7%).

Example 57

Resolution of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 50 mL three neck flask IPA (5 mL) and Dibenzoyl-L-tartaric acid monohydrate (1.84 g) were taken. It was heated to 60-65° C. 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.0 g, % purity-70%) dissolved in methanol (6 mL) was added into reaction mixture at 60-65° C. After 20 min. Dibenzoyl-L-tartaric acid salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (20 mg, % Chiral purity by HPLC of R-isomer 99.6%) was added as a seeding. It was stirred for 60 min. at 60-65° C. Solid salt was precipitated. It was gradually cooled to room temperature over a period of 2-3 h. The salt was filtered and washed with a mixture of IPA: MeOH (2:1). An enantiomerically enriched desired Dibenzoyl-L-tartaric acid salt of a mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained (Wt.-0.742 g, %Y-19.2%, Purity by HPLC-99.0%, % Chiral purity by HPLC of R-isomer 78.3%).

Example-58

Resolution of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 100 mL three neck flask IPA (25 mL) and Dibenzoyl-D-tartaric acid (8.8 g) were taken. It was heated to 60-65° C. 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (10 g, purity-91.8%) dissolved in methanol (30 mL) was added slowly into the reaction mixture at 60-65° C. It was stirred for 1 h at 60-65° C. Solid salt was precipitated. It was gradually cooled to room temperature and stirred for 3 h. The salt was filtered and washed with a mixture of IPA: MeOH (2:1). An enantiomerically enriched desired Dibenzoyl-D-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained (Wt.-7.2 g, %Y-38.4%, Purity by HPLC-98.2%, % Chiral purity by HPLC of S-isomer 71.7%).

Filtrate was collected and distilled out solvent under reduced pressure on Buchi rotavapour. Solid compound was obtained. Ethyl acetate (110 mL) was added. It was basified with aq. NaHCO₃.

It was transferred into a separating funnel. Ethyl acetate layer was separated and washed with water and brine solution. Ethyl acetate extract was collected and dried over anhydrous sodium sulfate. Ethyl acetate was distilled out to obtain a mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (wt.-5.62 g, % Purity by HPLC-84.5%). It was converted to Dibenzoyl-L-tartaric acid salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine by reacting a mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)-butan-2-amine (5.5 g) with Dibezoyl-L-tartaric acid monohydrate (5.0 g) as per the process described above in this example. (Wt.-4.2 g, % Y-40.1%, Purity by HPLC-98.1%, % Chiral purity by HPLC of R-isomer 84.8%).

Example-59

Process for the chiral enrichment of Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (1.0 g) (chiral purity of R-isomer-71.5%) was stirred with methanol (15 mL) at 60-65° C. for 1 h. Solid was filtered hot and washed with (5.0 mL) cold methanol. Solid mass obtained was dried and collected. Wt. of solid-0.763 g, chiral purity by HPLC of R-isomer-81%.

Example-60

Process for the chiral enrichment of Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (0.5 g) (chiral purity of R-isomer-77.5%) was stirred with a mixture of toluene (4 mL) and methanol (4 mL) at reflux temperature for 10-15 min. Reaction mixture was cooled to 25-30° C. Solid was filtered and washed with cold toluene. Solid mass obtained was dried and collected. Wt. of solid-0.490 g, chiral purity by HPLC of R-isomer-83.8%.

Example-61

Process for the chiral enrichment of Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine Dibenzoyl-L-tartaric acid salt of a mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.0 g) (chiral purity of R-isomer-71.6%) was stirred with a mixture of MIBK (10 mL) and methanol (10 mL) at reflux temperature for 60-90 min. Reaction mixture was cooled to 25-30° C. Solid was filtered and washed with a mixture of MIBK and methanol (1:1, 5.0 mL). Solid mass obtained was dried and collected. Wt. of solid-1.45 g, chiral purity by HPLC of R-isomer-80.8%.

Example-62

Process for the chiral enrichment of Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.0 g) (chiral purity of R-isomer-71.6%) was stirred with a mixture of 1,4-dioxane (10 mL) and methanol (10 mL)

at reflux temperature for 60-90 min. Reaction mixture was cooled to 25-30° C. It was stirred for 2 h. Solid was filtered and washed with a mixture of 1,4-dioxane and methanol (1:1, 5.0 mL). Solid mass obtained was dried and collected. Wt. of solid 0.945 g, chiral purity by HPLC of R-isomer-88.1%.

Example-63

Process for the chiral enrichment of Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.0 g) (chiral purity of R-isomer-78.4%) was stirred with a mixture of 1,4-dioxane (10 mL), methanol (10 mL) and 0.05 mL water at reflux temperature for 60-90 min. Reaction mixture was cooled to 25-30° C. It was stirred for 2 h. Solid was filtered and washed with a mixture of 1,4-dioxane and methanol (1:1, 5.0 mL). Solid mass obtained was dried and collected. Wt. of solid-1.25 g, chiral purity by HPLC of R-isomer-89.5%.

Example-64

Process for the chiral enrichment of Dibenzoyl-L-tartaric acid salt of mixture of (2R) and (2S)-4-oxo-4-[3-(trifluoro methyl)-5,6-dihydro[1,2,4]triazolo[4,3-a]pyrazin-7(8H)-yl]-1-(2,4,5-trifluorophenyl)butan-2-amine Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.0 g) (chiral purity of R-isomer-74.3%) was stirred with a mixture of DMF (1.5 mL) and IPA (6 mL) at 25-30° C. for 2.5 h. Solid was filtered and washed with IPA (2.0 mL). Solid mass obtained was dried and collected. Wt. of solid-0.64 g, chiral purity by HPLC of R-isomer-86.4%.

Example 65

Preparation of Dibenzoyl-L-TA Salt of Compound Formula (I)

The L-TA salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (wt.-4.0 g, % Purity by HPLC-97.5%, % Chiral purity by HPLC of R-isomer 98.6%) was added into ethyl acetate (20 mL). It was basified with satd. aq. NaHCO$_3$. It was transferred into a separating funnel. Ethyl acetate layer was separated and washed with water and brine solution. Ethyl acetate extract was collected and dried over anhydrous sodium sulfate. Ethyl acetate was distilled out to obtain a (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (Wt.-2.8 g, % Purity by HPLC-96.5%, % Chiral purity by HPLC of R-isomer 98.7%).

The crystalline form 3 of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine obtained is also characterized by an XPRD peaks at about 6.38, 8.00, 13.72, 17.91, 22.54, 25.44, 26.81°±0.2 degrees 2θ. The crystalline form 3 further characterized by an additional XPRD peaks at about 15.86, 16.05, 18.44, 19.44, 23.36°±0.2° degrees 2θ. (FIG. 3).

In a 25 mL round bottom flask Isopropanol (1.25 mL) and Dibenzoyl-L-tartaric acid monohydrate (0.462 g) were taken. It was heated to 60-65° C. 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (0.5 g) dissolved in methanol (1.0 mL) was added into reaction mixture at 60-65° C. over a period of 15 min. It was stirred for 15-30 min. at 60-65° C. Solid salt was precipitated. It was gradually cooled to room temperature and stirred for 30-60 min. The salt was filtered and washed with a mixture of IPA: MeOH (2:1, 3 mL). An enantiomerically enriched desired Dibenzoyl-L-tartaric acid salt off (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained (Wt.-0.358 g, %Y-37.8%, Purity by HPLC-97.5%, % Chiral purity by HPLC of R-isomer 99.6%). % of weight loss by TGA-4.7%. m.p.-156-160° C.

It is also characterized by an XPRD peaks at about 6.48, 7.98, 13.73, 15.98, 17.95, 22.59, 25.39°±0.2 degrees 2θ. The crystalline form further characterized by an additional XPRD peaks at about 5.50, 14.87, 18.66, 19.54, 20.28, 23.39, 25.65°±0.2° degrees 2θ. FIG. 2

Example 66

Resolution of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine using L-Tartaric acid In a 250 mL three neck flask MeOH (50 mL) and 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (5.0 g, % purity-94.3% and % H$_2$O-6.18%) were taken. To the clear solution L-tartaric acid (1.84 g) was added. It was heated to 60-65° C. and stirred for 3 h at 60-65° C. It was gradually cooled to room temperature and stirred for 16 h. It was cooled to 0-5° C. and stirred for 3 h. Small amount of solid salt was precipitated so, reaction mixture was concentrated up to 30 mL volume on a Buchi Rotavapour under reduced pressure. It was again stirred at 0-5° C. and stirred for 4 h. The salt was filtered and washed with IPA (10 mL). An enantiomerically enriched desired L-tartaric acid salt of mixture of (2R)-4-oxo-4-[3-(trifluoromethyl)-5,6-dihydro[1,2,4]triazolo[4,3-a] pyrazin-7(8H)-yl]-1-(2,4,5-trifluorophenyl)butan-2-amine was obtained (Wt.-2.19 g, %Y-32%, Purity by HPLC-97.4%, % Chiral purity by HPLC of R-isomer-97:4%, % H$_2$O-6.36%).

Example 67

Resolution of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine using L-Tartaric acid In a 250 mL three neck flask MeOH (12.5 mL) and 4-oxo-4-[3-(trifluoromethyl)-5,6-dihydro[1,2,4]triazolo[4,3-a] pyrazin-7(8H)-yl]-1-(2,4,5-trifluorophenyl)butan-2-amine (5.0 g, % purity-94.3% and % H$_2$O-6.18%) were taken. To the clear solution L-tartaric acid (1.84 g) was added. It was heated to 60-65° C. and stirred for 3 h at 60-65° C. Then isopropyl acetate (37.5 mL) was added. It was gradually cooled to room temperature and stirred for 18 h. solid salt was precipitated. The salt was filtered and washed with MeOH (5 mL). An enantiomerically enriched desired L-tartaric acid salt of mixture of (2R)-4-oxo-4-[3-(trifluoromethyl)-5,6-dihydro[1,2,4] triazolo[4,3-a]pyrazin-7(8H)-yl]-1-(2,4,5-trifluorophenyl)

butan-2-amine was obtained (Wt.-1.81 g, % Y-26.4%, Purity by HPLC-97.2%, % Chiral purity by HPLC of R-isomer-96.8%, % H$_2$O-5.7%).

Example 68

Resolution of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine using L-Tartaric acid In a 250 mL three neck flask MeOH (20 mL) and 4-oxo-4-[3-(trifluoromethyl)-5,6-dihydro[1,2,4]triazolo[4,3-a] pyrazin-7(8H)-yl]-1-(2,4,5-trifluorophenyl)butan-2-amine (5.0 g, % purity-94.0%) were taken. To the clear solution L-tartaric acid (1.84 g) was added. It was heated to 60-65° C. and stirred for 3 h at 60-65° C. Then IPA (33 mL) was added. It was gradually cooled to room temperature and stirred for 3 h. It was cooled to 0-5° C. and stirred for 2 h. solid salt was precipitated. The salt was filtered and washed with a mixture of IPA and MeOH (5:1, 10 mL). An enantiomerically enriched desired L-tartaric acid salt of mixture of (2R)-4-oxo-4-[3-(trifluoromethyl)-5,6-dihydro[1,2,4]triazolo[4,3-a] pyrazin-7(8H)-yl]-1-(2,4,5-trifluorophenyl)butan-2-amine was obtained (Wt.-2.12 g, % Y-31%, Purity by HPLC-97.8%, % Chiral purity by HPLC of R-isomer-93.6%).

Example 69

Resolution of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine using L-Tartaric acid In a 50 mL three neck flask IPA (45 mL) and 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.0 g, % purity-91.5% and % H$_2$O-5.93%) were taken. To the clear solution L-tartaric acid (0.735 g) dissolved in water (4.5 mL) was added at 50-55° C. It was heated to 60-65° C. and stirred for 22 h at 60-65° C. It was gradually cooled to room temperature and stirred for 6 h. It was cooled to 0-5° C. and stirred for 30 h. Solid salt was precipitated. The salt was filtered and washed IPA. An enantiomerically enriched desired L-tartaric acid salt of mixture of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained (Wt.-0.74 g, % Y-27%, Purity by HPLC-99.6%, % Chiral purity by HPLC of R-isomer-95%, % H$_2$O-7.14%).

Example 70

Resolution of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine Dibenzoyl-L-tartaric acid salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was prepared by reacting 4-oxo-4-[3-(trifluoromethyl)-5,6-dihydro[1,2,4] triazolo[4,3-a]pyrazin-7(8H)-yl]-1-(2,4,5-trifluorophenyl) butan-2-amine with Dibezoyl-L-tartaric acid monohydrate (1.18 molar equivalent) in IPA-methanol at 25-70° C. till solid mass precipitated out. The salt was filtered and washed with IPA; an enantiomerically enriched desired isomer was obtained. The salt was taken into ethyl acetate. It was basified with aq. NaHCO$_3$. Ethyl acetate layer was separated and washed with water and brine solution. Ethyl acetate extract was collected and dried over anhydrous sodium sulfate. Ethyl acetate was distilled out to obtain a mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (% Purity by HPLC-98%, % Chiral purity by HPLC of R-isomer 70%).

Example 71

Resolution of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine using S-(+)-O-acetyl mandelic acid In a 25 mL three neck flask WA (2.7 mL) and S-(+)-O-acetyl mandelic acid (0.47 g) were taken. To the clear solution 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (1.0 g, % purity-91.5%) was added at 60-65° C. It was stirred for 1 h at 60-65° C. It was gradually cooled to room temperature and stirred for 16 h. Distilled out solvent at reduced pressure to obtained crude solid S-(+)-O-acetyl mandelic acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine.

The salt (0.2 g) was stirred in a mixture of acetone (1.0 mL) and diisopropyl ether (5 mL) at room temperature for 16 h. Solid S-(+)-O-acetyl mandelic acid salt of mixture of (2R) and (2S)-4-oxo-4-[3-(trifluoromethyl)-5,6-dihydro[1,2,4] triazolo[4,3-a]pyrazin-7(8H)-yl]-1-(2,4,5-trifluorophenyl) butan-2-amine was filtered and washed with diisopropyl ether. Solid was dried under vacuum. (Wt.-40 mg, Purity by HPLC-98.0%, % chiral purity by HPLC of R-isomer-72.3%).

Example 72

Preparation of a mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate In a 25 mL round bottom flask isopropanol (4.0 mL) was taken. Then (2R:2S, 70:30)-4-oxo-4-[3-(trifluoromethyl)-5, 6-dihydro[1,2,4]triazolo[4,3-a]pyrazin-7(8H)-yl]-1-(2,4,5-trifluorophenyl)butan-2-amine (2.0 g) was added. The reaction mixture was heated at 70-75° C. Subsequently 85% Phosphoric acid (481 mg, 0.33 mL) was added over a period of 15-20 mins. Solid mass was precipitated out during addition. After a solvent mixture of water (1.8 mL) and IPA (14.0 mL) was added into the reaction mixture, keeping the temperature between 68-70° C. The slurry was aged for 2-3 h at 68-70° C. Then the slurry was cooled to room temperature. Solid mass was filtered off and washed with cold IPA. Solid mass was dried and collected. Wt. of titled compound-1.8 g. % Purity by HPLC-99.7%, % chiral purity by HPLC of R-isomer 72.8%.

Example-73

Process for the chiral enrichment of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate using IPA-Water (2R) and (2S)-4-oxo-4-[3-(trifluoromethyl)-5,6-dihydro [1,2,4]triazolo[4,3-a]pyrazin-7(8H)-yl]-1-(2,4,5-trifluorophenyl)butan-2-amine phosphate (2.0 g) (chiral purity of R-isomer-83%) was added into a mixture of Isopropanol (20.0 mL) and water (1.0 mL). The reaction mixture was heated to 80-85° C. for 1 to 1.5 hrs. The reaction mixture was cooled at 25-30° C. Solid was filtered and washed with cold IPA. Solid mass obtained was dried and collected. Wt. of solid-1.94 g, chiral purity by HPLC of R-isomer-93.32%.

Example-74

Process for the chiral enrichment of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate using Water-IPA (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate (1.0 g) (chiral purity of R-isomer-72.8%) was added into DM water (15.0 mL) and the reaction mixture was stirred at room temperature till clear solution was obtained. Subsequently Isopropanol (30.0 mL) was added. The reaction mixture was further stirred for 65-70 h at 25-30° C. Solid mass was precipitated out, which was filtered and washed with cold IPA (3.0 mL). Solid mass obtained was dried and collected. Wt. of solid-325 mg, % chiral purity by HPLC-54% Filterate was collected and concentrated under reduced pressure to obtain 650 mg of solid, HPLC chiral purity of R-isomer-82%.

Example-75

Process for the chiral enrichment of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate using DMSO-Ethanol (2R) and (2S)-4-oxo-4-[3-(trifluoromethyl)-5,6-dihydro [1,2,4]triazolo[4,3-a]pyrazin-7(8H)-yl]-1-(2,4,5-trifluorophenyl)butan-2-amine phosphate (1.0 g) (chiral purity of R-isomer-72.8%) was added into DMSO (50 mL) and the reaction mixture was stirred for 20-30 min. at 25-30° C. till clear solution was obtained. Subsequently ethanol (200 mL) was added. The reaction mixture was further stirred for 30-35 h at 25-30° C. Solid mass was precipitated out, which was filtered and washed with cold ethanol (5.0 mL). Solid mass obtained was dried and collected.
Wt. of solid-647 mg, % chiral purity by HPLC-57.8%. Filtrate (which contains R-isomer) was collected and analyzed, chiral purity by HPLC-96.6%.

Example-76

Process for the chiral enrichment of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate using DMSO-ethyl acetate (2R) and (2S)-4-oxo-4-[3-(trifluoromethyl)-5,6-dihydro [1,2,4]triazolo[4,3-a]pyrazin-7(8H)-yl]-1-(2,4,5-trifluorophenyl)butan-2-amine phosphate (1.0 g) (chiral purity of R-isomer-72%) was added into DMSO (10 mL) and the reaction mixture was warmed till clear solution was obtained. Then the reaction mixture was cooled to 25-30° C. To the solution ethyl acetate (5.0 mL) was added. The reaction mixture was stirred for 2-3 h at 25-30° C. Solid mass was precipitated out, which was filtered and washed with cold ethyl acetate (3.0 mL). Solid mass obtained was dried and collected.
Wt. of solid-567 mg, % chiral purity by HPLC-55.3%. Filtrate (which contains R-isomer) was collected and analyzed, % chiral purity by HPLC-96%.

Example-77

Process for the chiral enrichment of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate using DMSO-IPA (2R) and (2S)-4-oxo-4-[3-(trifluoromethyl)-5,6-dihydro [1,2,4]triazolo[4,3-a]pyrazin-7(8H)-yl]-1-(2,4,5-trifluorophenyl)butan-2-amine phosphate (1.0 g) (chiral purity of R-isomer-73%) was added into DMSO (10.0 mL) and the reaction mixture was warmed till clear solution was obtained. Then the reaction mixture was cooled to 25-30° C. To the solution isopropanol (10.0 mL) was added. The reaction mixture was stirred for 1-1.5 h at 25-30° C. Solid mass was precipitated out, which was filtered and washed with cold isopropanol (2.0 mL). Solid mass obtained was dried and collected.
Wt. of solid-600 mg, % chiral purity by HPLC-64.3%. Filtrate (which contains R-isomer) was collected and analyzed, % chiral purity by HPLC-92.6%

Example-78

Process for the chiral enrichment of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate using Water (2R) and (2S)-4-oxo-4-[3-(trifluoromethyl)-5,6-dihydro [1,2,4]triazolo[4,3-a]pyrazin-7(8H)-yl]-1-(2,4,5-trifluorophenyl)butan-2-amine phosphate (500 mg) (chiral purity of R-isomer-83%) was dissolved in water (2.5 mL) at 95-100° C. and stirred for 0.5-1 h. Then the reaction mixture was cooled to 25-30° C. and further stirred for 3-4 h. Solid mass was precipitated out, which was filtered and washed with cold water (2.0 mL). Solid mass obtained was dried and collected. Wt. of solid-159 mg, % chiral purity by HPLC-92%.

Example 79

Preparation of (2R)-4-oxo-4-[3-(trifluoromethyl)-5, 6-dihydro[1,2,4]triazolo[4,3-a]pyrazin-7(8H)-yl]-1-(2,4,5-trifluorophenyl)butan-2-amine phosphate\salt from Racemic 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 500 mL three neck flask IPA (125 mL) and Dibenzoyl-L-tartaric acid monohydrate (46.2 g) were taken. It was heated to 60-65° C. 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (50 g, % purity-91.8%) dissolved in methanol (150 mL) was added into reaction mixture at 60-65° C. over a period of 45 min. It was stirred for 60 min. at 60-65° C. Solid salt was precipitated. It was gradually cooled to room temperature and stirred for 3 h. The salt was filtered and washed with a mixture of IPA: MeOH (2:1, 100 mL). An enantiomerically enriched desired Dibenzoyl-L-tartaric acid salt of mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained (Wt.-

33.6 g, % Y-34.9%, Purity by HPLC-98.8%, % Chiral purity by HPLC of R-isomer 75.7%).

The salt (25 g) was added into ethyl acetate (250 mL). It was basified with satd. aq. NaHCO₃. It was transferred into a separating funnel. Ethyl acetate layer was separated and washed with water and brine solution. Ethyl acetate extract was collected and dried over anhydrous sodium sulfate. Ethyl acetate was distilled out to obtain a mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (wt.-12.6 g, % Purity by HPLC-98.9%, % Chiral purity by HPLC of R-isomer 74.5%).

In a 250 mL round bottom flask isopropanol (25 mL) was taken. Then (2R:2S, 74.5:24.5)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (12.6 g) was added at room temperature. It was stirred for 10-15 min. at room temperature. To the solution water (11.3 mL) was added. Subsequently 85% aq. Phosphoric acid (481 mg, 0.33 mL) was added over a period of 15-20 mins. It was heated at 68-70° C. and stirred for 2 h. The mixture was cooled to room temperature; solid mass was precipitated. After that IPA (88 mL) was added into the reaction mixture. The slurry was aged for 24 h at room temperature (25-30° C.) Solid mass was filtered off and washed with cold IPA. Solid mass was dried and collected. Wt. of a mixture of (2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate.-13.6 g. % Y-87%, % Purity by HPLC-99.8%, % Chiral purity by HPLC of R-isomer 73.0%.

(2R) and (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate (5.0 g) (chiral purity of R-isomer-73%) was dissolved in DMSO (20 mL) at 50-55° C. It was cooled to room temperature and stirred for 20 h. Solid mass was precipitated. To the slurry ethanol (2.5 mL) was added and stirred for 2 h at room temperature. Solid was filtered and washed with cold WA. Solid mass obtained was dried and collected. Wt. of solid-2.54 g. Filtrate was taken in a 100 mL three neck flask. Then IPA (50 mL) was added and stirred for 18 h at room temperature. Solid mass was precipitated. Solid was filtered and washed with cold IPA. Solid mass obtained was dried and collected. Wt. of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate-1.7 g. % Purity by HPLC-98%, chiral purity by HPLC of R-isomer-95.6%, % H₂O-0.19%, m. p. 209-211° C. and SOR (1% in water)-(−)20.8°.

Example 80

Preparation of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate salt from (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine L-TA salt The L-TA salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (wt.-4.0 g, % Purity by HPLC-93.9%, % Chiral purity by HPLC of R-isomer 93.5%) was added into ethyl acetate (20 mL). It was basified with satd. aq. NaHCO₃. It was transferred into a separating funnel. Ethyl acetate layer was separated and washed with water and brine solution. Ethyl acetate extract was collected and dried over anhydrous sodium sulfate. Solvent was distilled out to obtain a (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (Wt.-2.4 g, % Purity by HPLC-98.6%, % Chiral purity by HPLC of R-isomer 94.0%).

In a 50 mL round bottom flask isopropanol (5 mL) was taken. Then (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.4 g) was added at room temperature. It was stirred for 10-15 min. at room temperature. To the solution water (2.16 mL) was added. Subsequently 85% aq. Phosphoric acid (0.57 g, 0.33 mL) was added over a period of 15-20 mins. It was heated at 68-72° C. and stirred for 2 h. It was cooled to room temperature and stirred for 3 h, solid mass was precipitated. After that, IPA (17 mL) was added into the reaction mixture. The slurry was aged for 20 h at room temperature (25-30° C.). Solid mass was filtered off and washed with cold IPA. Solid mass was dried and collected. Wt. of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate-1.92 g. % Y-66%, % H₂O-0.22%, % Purity by HPLC-99.1%, % Chiral purity by HPLC of R-isomer-91.5%.

Filtrate was collected. Distilled out solvent to dryness. Solid (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate hydrated was obtained. [Wt.-0.93 g. % Y-34%, % H₂O-4.97%, % Purity by HPLC-96.2%, % Chiral purity by HPLC of R-isomer-98.9%].

Example 81

Preparation of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate salt from (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine L-TA salt The L-TA salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (wt.-5.0 g, % Purity by HPLC-97.0%, % Chiral purity by HPLC of R-isomer 95.2%) was added into ethyl acetate (20 mL). It was basified with satd. aq. NaHCO₃. It was transferred into a separating funnel. Ethyl acetate layer was separated and washed with water and brine solution. Ethyl acetate extract was collected and dried over anhydrous sodium sulfate. Solvent was distilled out to obtain a (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (wt.-3.0 g, % Purity by HPLC-97.2%, % Chiral purity by HPLC of R-isomer 94.0%).

In a 50 mL round bottom flask Isopropanol (5 mL) and water (2.7 mL) were taken. Then (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (3.0 g) was added at room temperature. It was cooled to 20° C. To the solution 85% aq. Phosphoric acid (0.84 g, 0.5 mL) was added over a period of 15-20 mins. It was stirred at 18-20° C. for 7 h. After that IPA (21 mL) was added into the reaction mixture. It was aged for 24 h at 18-20° C. Solid mass was precipitated. Solid mass was filtered off and washed with cold IPA (15 mL). Solid mass was dried and collected. Wt. of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate-2.64 g. % Y-68.5%, % H₂O-0.63%, % Purity by HPLC-99.2%, % Chiral purity by HPLC of R-isomer-93.5%.

It is also characterized by an XPRD peaks at about 4.6, 13.84, 15.05, 18.21, 24.25°±0.2 degrees 2θ. The anhydrous crystalline form further characterized by an additional XPRD peaks at about 13.45, 14.28, 15.52, 18.52, 19.09, 21.92, 23.63, 25.36, 26.67°±0.2° degrees 2θ FIG. 5

Example 82

Preparation of (2S) and (2R) N-trifluoroacetyl-4-oxo-4-[3-(trifluoromethyl)-5,6-dihydro[1,2,4]triazolo[4,3-a]pyrazin-7(8H)-yl]-1-(2,4,5=trifluorophenyl)butan-2-amine In a 50 mL three neck flask (2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (wt.-1.0 g, % Purity by HPLC-92.2%, % Chiral purity by HPLC of S-isomer 91.0%) and dichloromethane (20 mL) were taken. It was cooled to −5 to 0° C. To the reaction mixture triethylamine (0.750 g) was added. Then trifluoroacetic anhydride (0.775 g) was added drop by drop over a period of 15 min. at −5 to 0° C. After 1 h, reaction mixture was dumped into cold water (20 mL). It was transferred into a separating funnel. The organic layer was separated and washed with water and brine solution. It dried over anhydrous sodium sulfate. Distilled out solvent to obtain a (2S) N-trifluoroacetyl-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (Wt.-1.16 g, % Purity by HPLC-96.5%).

Example 83

Preparation of (2R/S) 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 25 mL three neck flask (2S) N-trifluoroacetyl-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (wt.-0.250 g, % Purity by HPLC-96.5%) was dissolved in a mixture of MeOH (2.5 mL) and water (0.5 mL) at 25-30° C. To the reaction mixture lithium hydroxide monohydrate (21 mg) was added. It was stirred at 0 to 5° C. for 4 h and at 25 to 30° C. for 24 h. Distilled out solvent at reduced pressure on Buchi rotavapour. To the thick liquid water (2.5 mL) was added. It was transferred into a separating funnel. It was extracted twice with ethyl acetate. Both the extracts were combined and washed with water and brine solution. It was dried over anhydrous sodium sulfate. Distilled out solvent to obtain a 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (Wt.-78 mg, % Purity by HPLC-83.1%).

Example 84

Preparation of (E/Z)-3-(benzylamino)-1-(3-(trifluoromethyl)-5,6-dihydro-[1,2,4]triazolo[4,3-a]pyrazin-7(8H)-yl)-4-(2,4,5-trifluorophenyl)but-2-en-1-one In a 50 mL round bottom flask Sodium salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one (2.0 g), WA (10 mL) and acetic acid (0.3 mL) were charged. To the reaction mixture benzyl amine (0.5 g) was added at 25-30° C. It was heated to 35-40° C. and stirred for 10 h. After that benzyl amine (0.25 g) was added. Then it was heated to reflux temperature and stirred for 14 h, during that at every 5 h interval benzyl amine (0.25 g) was added. Distilled out the solvent at reduced pressure. To the thick liquid water (10 mL) and ethyl acetate) were added. It was transferred into a separating funnel. Ethyl acetate layer was collected. It was washed with dil. aq. acetic acid, saturated aq. sodium bicarbonate solution, water and brine solution. It was dried over anhydrous sodium sulfate. Distilled out solvent to obtain a (E/Z)-3-(benzylamino)-1-(3-(trifluoromethyl)-5,6-dihydro-[1,2,4]triazolo[4,3-a]pyrazin-7(8H)-yl)-4-(2,4,5-trifluorophenyl)but-2-en-1-one (Wt.-1.73 g)

Example-85

Preparation of 3-hydroxy-1-(3-(trifluoromethyl)-5,6-dihydro-[1,2,4]triazolo[4,3-a]pyrazin-7(8H)-yl)-4-(2,4,5-trifluorophenyl)butan-1-one In a 500 mL round bottom flask THF (50 mL) and methanol (100 mL) were taken. To the solution sodium salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one (2.0 g) was added. It was cooled to −78 to 70° C. in a dry-ice bath. Then NaBH$_4$ (0.7 g) was added in small lots in 10-15 min. It was stirred at −78 to 70° C. for 3-4 h. Reaction mixture was poured into aq. saturated NH$_4$Cl solution at 0-5° C. Product was extracted with ethyl acetate. Organic layer was collected and dried over anhydrous sodium sulfate. Solvent was evaporated at reduced pressure to obtain the product. (Wt.-2.0 g, % Y-100%, % Purity by HPLC-95.6%).

$^1$H NMR (300 MHz, CDCl$_3$): δ 2.57-2.66 (m, 2H), 2.83-2.84 (m, 2H), 3.95-4.16 (m, 3H), 4.24-4.33 (m, 2H), 4.86-4.95 (m, 2H), 6.86-6.94 (m, 1H), 7.10-7.19 (m, 1H).

$^{13}$CNMR (75.4 MHz, CDCl$_3$): δ 34.8, 35.0, 38.9, 39.07, 41.6, 42.3, 43.1, 43.5, 67.7, 105.2, 116.2, 119.2, 120.9, 143.1, 144.8, 147.0, 148.0, 149.4, 150.3, 154.3, 157.5, 170.7, 171.1 (Assignment are denoted for major/minor/both isomers)
IR (cm$^{-1}$): 3387, 1649 ESI-MS: 430.8 (M+Na)$^+$

Example 86

Preparation of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 250 mL round bottom flask THF (225 mL) was taken. It was cooled to less than −5° C. and NaBH$_4$ (5.62 g) was added. After that methanesulfonic acid (17.8 g) was added dropwise at less than −5° C. over a period of 30 min. 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine (20.0 g) is mixed in a solvent mixture of THF (50 mL) and IPA (22 mL) and added into the reaction mixture, keeping the temperature below 0° C. It was stirred for 4-6 h below 5° C. After usual work-up procedure, product was extracted in a suitable solvent. Extract was washed and dried over anhydrous sodium sulfate. Solvent was evaporated at reduced pressure to obtain the product. (Wt.-20.8 g, % Purity by HPLC-80.7% and % of 3-hydroxy-1-(3-(trifluoromethyl)-5,6-dihydro-[1,2,4]triazolo[4,3-a]pyrazin-7(8H)-yl)-4-(2,4,5-trifluorophenyl)butan-1-one by HPLC-15.5%).

Example-87

Preparation of phosphate salt of (2R) 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 25 mL round bottom flask Isopropanol (1 mL) and (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (0.5 g) were taken at room temperature. Then to the solution 85% aq. Phosphoric acid (0.144 g) mixed with IPA (1 mL) was added over a period of 15-20 mins. It was heated to 75° C. and stirred for 10-15 min. After that it was cooled to 65° C. and stirred for 2 h at 65-70° C. Solid mass was precipitated. It was cooled to room temperature. Sticky solid was obtained on addition of IPA so, water (0.4 mL) was added, into the reaction mixture and heated to 80-85° C. After 15 min. it was cooled to room temperature and stirred for 20 h. Solid mass was filtered off and washed with cold IPA (15 mL). Solid mass was dried and collected. Wt. of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate-0.297 g. % Y-48.1%, % weight loss by TGA-2.94%, % Purity by HPLC-99.5%, % Chiral purity by HPLC of R-isomer-97.9%.

It is also characterized by an XPRD peaks at about 4.61, 6.50, 7.93, 9.30, 13.68, 15.88, 22.54, 25.33, 26.97°±0.2 degrees 2θ. The crystalline form further characterized by an additional XPRD peaks at about 13.99, 15.12, 18.63, 19.22, 21.93, 23.38, 25.61°±0.2° degrees 2θ. (FIG. 6).

We claim:

1. A process for the preparation of compound of formula (I) or its salts comprising,

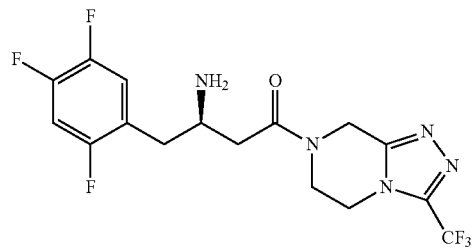
(I)

a) reacting trifluorophenylacetic acid (II) or its acid chloride with Meldrum's acid and 3-trifluoromethyl 5,6,7,8-tetrahydro[1,2,4]triazolo[4,3-a]pyrazine.HCl of formula (III) in presence of a suitable base and suitable acid, which is further converted to the compound of a formula (IV) by reacting with suitable alkali and alkali earth metals in suitable solvent

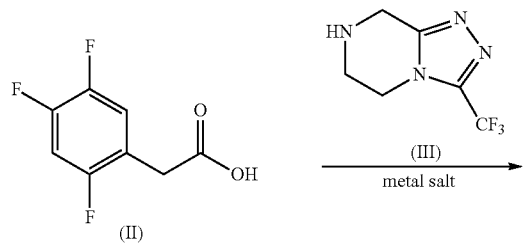

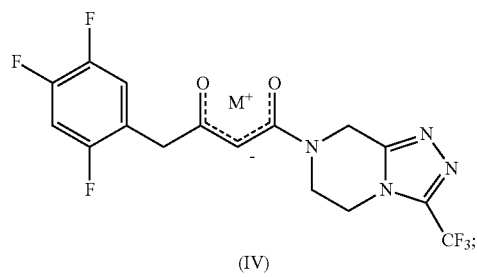
(IV)

Wherein $M^+$ = Na, K, Li, Ca, Mg, Cu, Cs b) reacting the compound of formula (IV) with suitable ammonia source or with a suitable organic amine in a suitable solvent and optionally in the presence of a suitable acid to obtain the compound of formula (V)

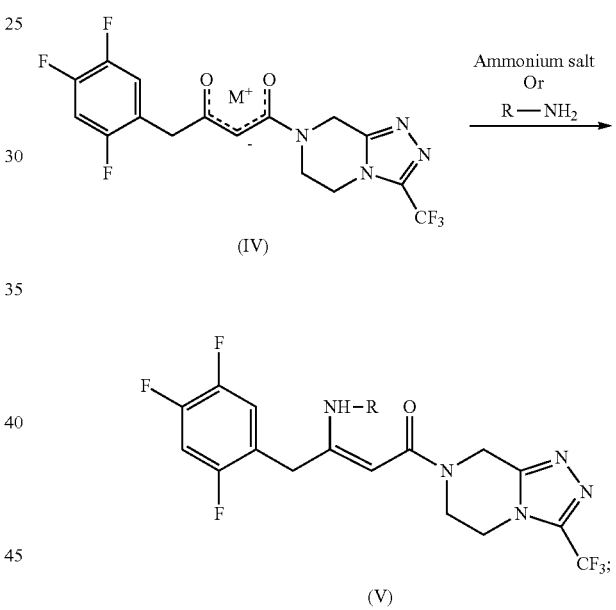

Where, R = H or protecting group
Wherein $M^+$ = Na, K, Li, Ca, Mg, Cu, Cs c) reducing the compound of formula (V) by using suitable borane containing reducing agent optionally in the presence of an acid in a suitable solvents to obtain racemic compound of formula (VI)

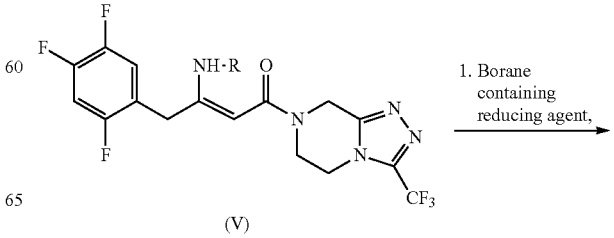

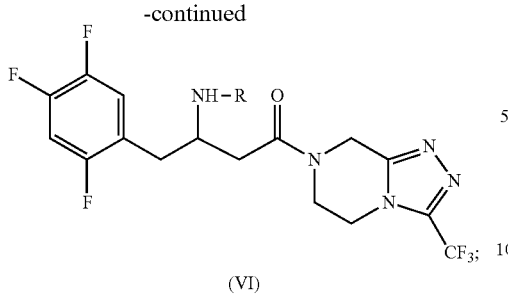

(VI)

Where, R = H or protecting group

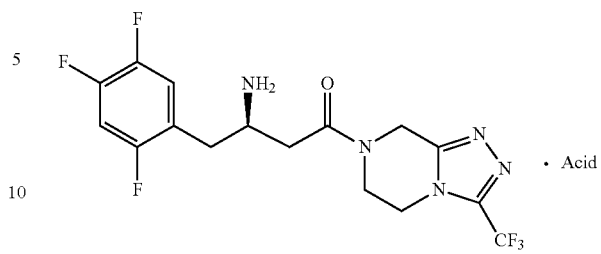

(Ia)

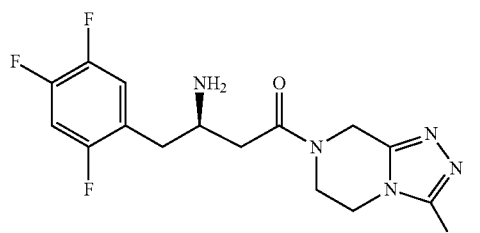

(Ib)

d) resolution of the compound formula (VI) by suitable chiral resolving agents in suitable solvents to obtain the diastereomeric salt of compound of formula (I)

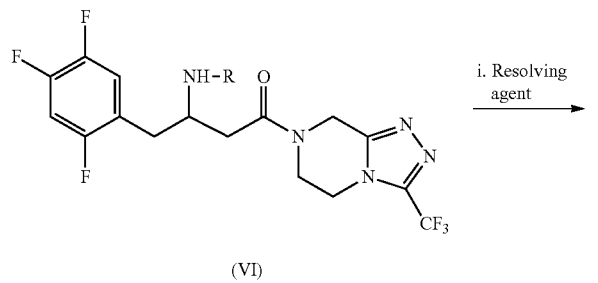

i. Resolving agent

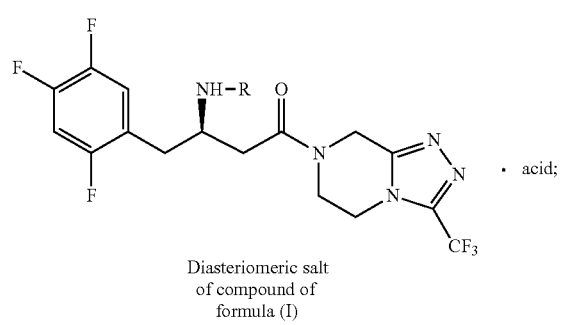

Diasteriomeric salt of compound of formula (I)

Where, R = H or protecting group e) optionally, deprotecting the compound of formula (VI) (Wherein R≠H) prior to resolution;

f) converting the diastereomeric salt of compound of formula (I), with suitable base in presence of suitable solvents to obtain compound of formula (I);

g) optionally preparing a salt of formula (I), as formula (Ib), having at least 70% chiral purity, by reacting the compound of formula (I) with a suitable acid(s) in a suitable solvent(s), with the salt further converted to the compound of formula (Ia), having at least 90% chiral purity, by suitable chiral enrichment 2. The process according to claim 1 in step (a), wherein the suitable alkali and alkali earth metal is selected from hydroxides, chlorides, carbonate, acetates, sulfates, nitrates and oxides, the suitable solvent used is selected from esters; hydrocarbons or halogenated hydrocarbons, DMF, DMSO, DMAc, NMP, acetonitrile or mixtures thereof, the suitable base is selected from triethyl amine, di isopropyl ethyl amine, dimethylamino pyridine, DMF, collidine, imidazole, pyridine, N,N-dimethyl aniline or mixtures thereof and the suitable acid used is HCl, HBr, $H_2SO_4$, Poly phosphoric acid, trichloroacetic acid, trifluoroacetic acid, $CH_3SO_3H$, $CF_3SO_3H$, p-toluene sulfonic acid, benzenesulfonic acid, camphorsulfonic acid, acetic acid, formic acid, pivalic acid.

3. The process according to claim 1 in step (b), wherein suitable ammonia source is selected from ammonium acetate, ammonium carbonate, ammonium hydroxide, ammonium formate, ammonium lactate, ammonium citrate dibasic, ammonium carbamate, ammonium benzoate and suitable organic amines is selected from benzylamine or α-methylphenethyl amine and suitable solvent used is selected from water, suitable alcohols; ethers; or suitable esters or their suitable mixtures.

4. The process according to claim 1 in step (c), wherein the suitable borane containing reagent used is selected from $BH_3$ complexes selected from $BH_3$-ammonia, $BH_3$-t-Bu amine, $BH_3$-triethylamine, $BH_3$-trimethylamine, $BH_3$-pyridine, $BH_3$-pyrrole, $BH_3$-piperazine, $BH_3$-piperidine; borane ether complex; borane phosphine complexes; borane sulfide complexes, suitable acid used is selected from inorganic or organic acid selected from HCl, $H_2SO_4$; or organic acids selected from lower alkyl acid selected from $CH_3COOH$, $CH_3CH_2COOH$; lower haloalkyl acid selected from $CF_3COOH$, dichloroacetic acid; phenyl or substituted phenyl acid selected from benzoic acid; loweralkyl sulfonic acid selected from $CH_3SO_3H$, $C_2H_5SO_3H$; haloalkyl sulfonic acid selected from $CF_3SO_3H$; phenyl sulfonic acid selected from $C_6H_5SO_3H$; loweralkyl substituted phenyl sulfonic acid or naphthyl sulfonic acid; phosophoric acid, lower alkyl phosphonic acid selected from methylphosphonic acid, phenylphosphonic acid, $BF_3.OEt_2$, tartaric acid, modified tartaric acid, camphorsulfonic acid and suitable solvent used is selected from suitable alcohols; ethers; aprotic polar solvents or their suitable mixtures.

5. The process according to claim 1 in step (d), wherein the suitable resolving agent used is selected from tartaric acid, dibenzoyltartaric acid, o-nitrobenzoyl tartaric acid, lactic acid, 10-camphorsulfonic acid, 8-camphorsulfonic acid, malic acid, mandelic acid, o-acetylmandelic acid, o-methylmandelic acid, and the suitable solvent used is selected from water, suitable alcohols; esters; chlorinated solvents selected from chloroform, dichloromethane; nitriles; hydrocarbons; ketones; ethers; aprotic polar solvents; or their suitable mixtures.

6. The process according to claim 1 in step (d), which comprises preparation of diastereomeric salt of compound formula (I) obtained with chiral purity of at least 70%.

7. The process according to claim 1 in step (f), which comprises formation of compound formula (I), wherein the suitable base used is selected from alkali or alkali metal hydroxides; or alkali metal carbonates, the suitable solvent used is selected from alcohols selected from methanol, ethanol, isopropanol, butanol, 1,2-dimethoxy ethanol, 2-methoxy ethanol, 2-ethoxy ethanol, isoamyl alcohol and ethylene glycol; esters selected from ethyl acetate and isopropyl acetate; chlorinated solvents selected from chloroform, dichloromethane; nitriles selected from acetonitrile; hydrocarbons selected from hexane, heptane, toluene, xylene, chlorobenzene; ketones selected from acetone, methyl ethyl ketone; ethers selected from diethyl ether, 1,4-dioxane, DIPE, MTBE, THF; aprotic polar solvents selected from DMF, DMSO, DMA, water and their suitable mixtures.

8. A process for the preparation of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine of formula (I) or its salts comprising,

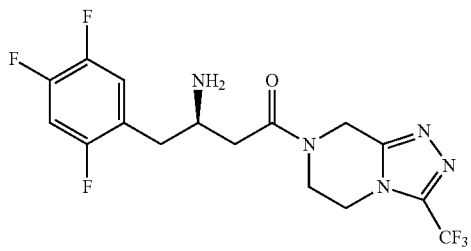 [SMILES: N[C@@H](CC(=O)N1CCn2c(nnc2C(F)(F)F)C1)Cc1cc(F)c(F)cc1F]

a) reacting trifluorophenylacetic acid (II), Meldrum's acid and 5,6,7,8-tetrahydro[1,2,4]triazolo[4,3-a]pyrazine-.HCl compound (III) in presence of a suitable base and suitable acid, and further converting (III) to the compound of a formula (IV) by reacting with suitable metals salts

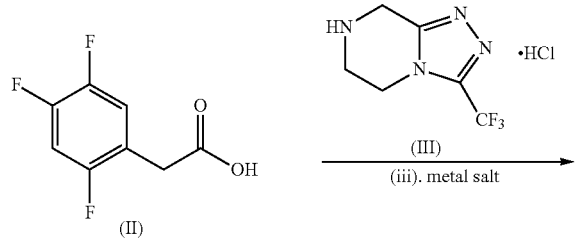

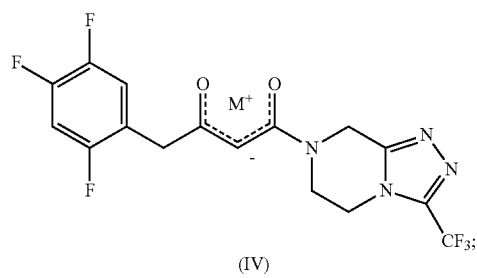

Wherein $M^+$ = Na, K, Li, Ca, Mg, Cu, Cs b) reacting compound of formula (IV) with suitable ammonium source in a suitable solvent in the presence of a suitable acid to obtain 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine

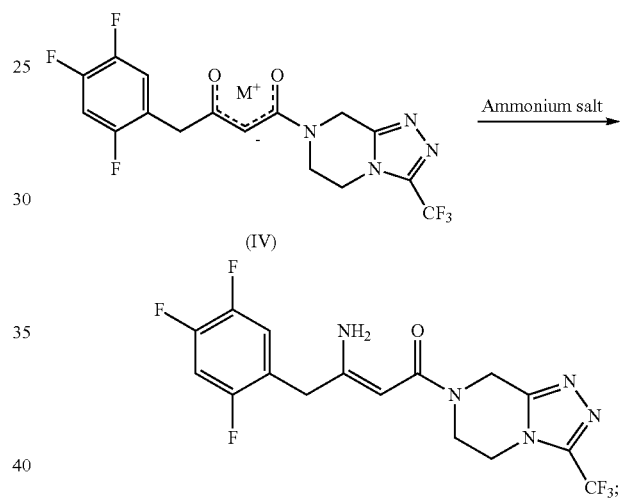

Wherein $M^+$ = Na, K, Li, Ca, Mg, Cu, Cs c) reducing the 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine by using suitable borane containing reducing agent optionally in presence of an acid in a suitable solvent to obtain racemic 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine

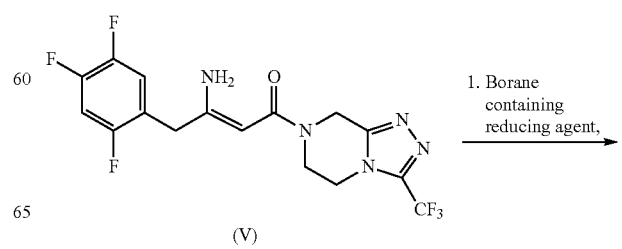

-continued

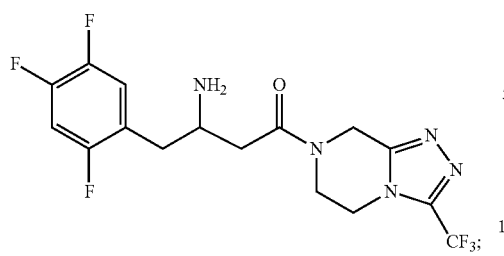

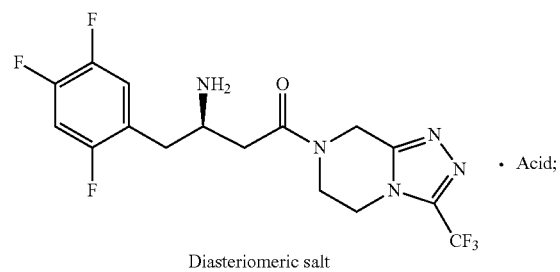

Diasteriomeric salt d) resolution of racemic 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine by a suitable chiral resolving agents in a suitable solvent to obtain diastereomeric salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine

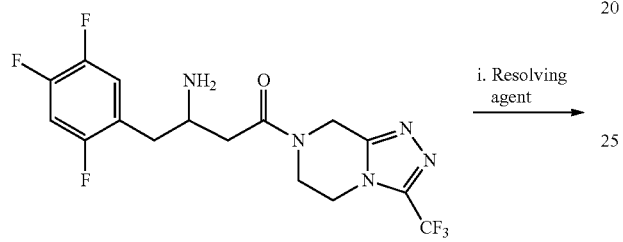

i. Resolving agent e) converting a diastereomeric salt obtained in step-(d) to compound of formula (I) by using suitable base in presence of suitable solvent;

f) optionally preparation of suitable salts of (2R)-(−)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine by reacting with a suitable acid(s) in a suitable solvent.

\* \* \* \* \*